United States Patent
Schuele et al.

(10) Patent No.: US 12,042,228 B2
(45) Date of Patent: Jul. 23, 2024

(54) CONFOCAL LASER EYE SURGERY SYSTEM

(71) Applicant: AMO Development, LLC, Irvine, CA (US)

(72) Inventors: Georg Schuele, Portola Valley, CA (US); Noah Bareket, Saratoga, CA (US); David Dewey, Sunnyvale, CA (US); John S. Hart, Menlo Park, CA (US); Javier G. Gonzalez, Palo Alto, CA (US); Raymond Woo, Palo Alto, CA (US); Thomas Z. Teisseyre, Pacifica, CA (US); Jeffrey A. Golda, Menlo Park, CA (US); Katrina B. Sheehy, Redwood City, CA (US); Madeleine C O'Meara, San Francisco, CA (US); Bruce Woodley, Palo Alto, CA (US)

(73) Assignee: AMO Development, LLC, Irvine, CA (US)

( * ) Notice: Subject to any disclaimer, the term of this patent is extended or adjusted under 35 U.S.C. 154(b) by 0 days.

(21) Appl. No.: 17/645,747

(22) Filed: Dec. 23, 2021

(65) Prior Publication Data

US 2022/0110520 A1 Apr. 14, 2022

Related U.S. Application Data

(62) Division of application No. 16/188,119, filed on Nov. 12, 2018, now Pat. No. 11,229,357, which is a (Continued)

(51) Int. Cl.
*A61B 3/117* (2006.01)
*A61B 3/00* (2006.01)
(Continued)

(52) U.S. Cl.
CPC .......... *A61B 3/1173* (2013.01); *A61B 3/1025* (2013.01); *A61B 3/14* (2013.01);
(Continued)

(58) Field of Classification Search
CPC ... A61B 3/0025; A61B 3/1025; A61B 3/1173; A61B 3/14; A61F 2009/00844;
(Continued)

(56) References Cited

U.S. PATENT DOCUMENTS

| | | |
|---|---|---|
| 5,177,511 A | 1/1993 | Feuerstein et al. |
| 5,720,894 A | 2/1998 | Neev et al. |

(Continued)

FOREIGN PATENT DOCUMENTS

| | | |
|---|---|---|
| CN | 2762415 Y | 3/2006 |
| EP | 2057973 A1 | 5/2009 |

(Continued)

OTHER PUBLICATIONS

Lynch., et al., "Beam Manipulation: Prism vs. Mirrors", Originally published in Germany on Nov. 12, 2009, Photonik, pp. 45-47.

*Primary Examiner* — Jonathan T Kuo
*Assistant Examiner* — Vynn V Huh
(74) *Attorney, Agent, or Firm* — Johnson & Johnson Surgical Vision, Inc.

(57) ABSTRACT

A laser surgery system includes a light source, an eye interface device, a scanning assembly, a confocal detection assembly and preferably a confocal bypass assembly. The light source generates an electromagnetic beam. The scanning assembly scans a focal point of the electromagnetic beam to different locations within the eye. An optical path propagates the electromagnetic beam from a light source to the focal point, and also propagates a portion of the electromagnetic beam reflected from the focal point location back along at least a portion of the optical path. The optical (Continued)

path includes an optical element associated with a confocal detection assembly that diverts a portion of the reflected electromagnetic radiation to a sensor. The sensor generates an intensity signal indicative of intensity the electromagnetic beam reflected from the focal point location. The confocal bypass assembly reversibly diverts the electromagnetic beam along a diversion optical path around the optical element.

1 Claim, 27 Drawing Sheets

Related U.S. Application Data division of application No. 14/576,593, filed on Dec. 19, 2014, now Pat. No. 10,123,696.

(60) Provisional application No. 62/043,749, filed on Aug. 29, 2014, provisional application No. 61/970,854, filed on Mar. 26, 2014.

(51) Int. Cl.
| | |
|---|---|
| A61B 3/10 | (2006.01) |
| A61B 3/14 | (2006.01) |
| A61F 9/007 | (2006.01) |
| A61F 9/008 | (2006.01) |

(52) U.S. Cl.
CPC .......... A61F 9/00754 (2013.01); A61F 9/008 (2013.01); *A61B 3/0025* (2013.01); *A61F 2009/00844* (2013.01); *A61F 2009/00878* (2013.01); *A61F 2009/00897* (2013.01)

(58) Field of Classification Search
CPC .. A61F 2009/00878; A61F 2009/00897; A61F 9/00754; A61F 9/008
USPC ........................................ 606/2–19
See application file for complete search history.

(56) References Cited

U.S. PATENT DOCUMENTS

| 5,825,533 | A | 10/1998 | Yonezawa |
| 5,957,915 | A | 9/1999 | Trost |
| 5,984,916 | A | 11/1999 | Lai |
| 6,019,472 | A | 2/2000 | Koester et al. |
| 6,454,761 | B1 | 9/2002 | Freedman |
| 6,577,394 | B1 | 6/2003 | Zavislan |
| 7,554,654 | B2 | 6/2009 | Meeks et al. |
| 7,655,002 | B2 | 2/2010 | Myers et al. |
| 7,717,907 | B2 | 5/2010 | Ruiz et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,414,564 | B2 | 4/2013 | Goldshleger et al. |
| 8,451,446 | B2 | 5/2013 | Garab et al. |
| 2002/0167655 | A1 | 11/2002 | Friedman et al. |
| 2003/0025842 | A1 | 2/2003 | Saccomanno |
| 2004/0012853 | A1* | 1/2004 | Garcia ............... G02B 21/0068 |
| | | | 359/489.08 |
| 2004/0095573 | A1 | 5/2004 | Tsai et al. |
| 2004/0102765 | A1 | 5/2004 | Koenig |
| 2007/0123761 | A1 | 5/2007 | Daly et al. |
| 2007/0282313 | A1 | 12/2007 | Huang et al. |
| 2010/0130966 | A1 | 5/2010 | Brownell |
| 2010/0137849 | A1 | 6/2010 | Hanft et al. |
| 2011/0172649 | A1 | 7/2011 | Schuele et al. |
| 2011/0251601 | A1* | 10/2011 | Bissmann ........... A61F 9/00831 |
| | | | 606/5 |
| 2011/0319873 | A1 | 12/2011 | Raksi et al. |
| 2011/0319875 | A1 | 12/2011 | Loesel et al. |
| 2012/0165798 | A1 | 6/2012 | Rathjen |
| 2013/0103014 | A1 | 4/2013 | Gooding et al. |
| 2013/0158530 | A1 | 6/2013 | Goldshleger et al. |
| 2013/0201448 | A1 | 8/2013 | Nozato |
| 2013/0338648 | A1 | 12/2013 | Hanebuchi et al. |
| 2014/0058367 | A1 | 2/2014 | Dantus |
| 2014/0104576 | A1 | 4/2014 | Bor et al. |
| 2014/0128731 | A1 | 5/2014 | Gonzalez et al. |
| 2014/0128821 | A1 | 5/2014 | Gooding et al. |
| 2014/0128853 | A1 | 5/2014 | Angeley et al. |
| 2014/0157190 | A1 | 6/2014 | Kim et al. |
| 2014/0163534 | A1 | 6/2014 | Angeley et al. |
| 2014/0276671 | A1 | 9/2014 | Gooding |
| 2014/0316389 | A1 | 10/2014 | Schuele et al. |
| 2014/0362882 | A1 | 12/2014 | Sgandurra et al. |
| 2015/0272782 | A1 | 10/2015 | Schuele et al. |
| 2016/0235588 | A1 | 8/2016 | Hart et al. |
| 2016/0250068 | A1 | 9/2016 | Dewey et al. |

FOREIGN PATENT DOCUMENTS

| WO | 02088818 | A1 | 11/2002 |
| WO | 2007143111 | A2 | 12/2007 |
| WO | 2009033110 | A2 | 3/2009 |
| WO | 2009040591 | A1 | 4/2009 |
| WO | 2011091326 | A1 | 7/2011 |
| WO | 2011116306 | A2 | 9/2011 |
| WO | 2012135073 | A2 | 10/2012 |
| WO | 2014149774 | A2 | 9/2014 |
| WO | 2014158615 | A1 | 10/2014 |
| WO | 2014163891 | A1 | 10/2014 |

* cited by examiner

```
┌─────────────────────────────────────────────────────────────────────┐
│ USING THE SECOND SUPPORT ASSEMBLY TO SUPPORT A SECOND REFLECTOR     │─222
│ CONFIGURED TO REFLECT THE ELECTROMAGNETIC RADIATION BEAM TO         │
│ PROPAGATE ALONG A PORTION OF THE VARIABLE OPTICAL PATH SO AS TO     │
│ BE INCIDENT ON THE FIRST REFLECTOR                                  │
└─────────────────────────────────────────────────────────────────────┘
                                  ▼
┌─────────────────────────────────────────────────────────────────────┐
│ USING THE SENSOR GENERATE THE INTENSITY SIGNAL COMPRISES PASSING    │─224
│ A REFLECTED PORTION OF THE ELECTROMAGNETIC RADIATION BEAM THROUGH   │
│ AN APERTURE TO BLOCK PORTIONS OF THE ELECTROMAGNETIC REDIATION      │
│ BEAM REFLECTED FROM LOCATIONS OTHER THAN THE FOCAL POINT LOCATION   │
└─────────────────────────────────────────────────────────────────────┘
```

FIG. 5

```
┌─────────────────────────────────────────────────────────────────────┐
│ PASSING THE ELECTROMAGNETIC RADIATION BEAM THROUGH A                │─226
│ POLARIZATION-SENSITIVE DEVICE                                       │
└─────────────────────────────────────────────────────────────────────┘
                                  ▼
┌─────────────────────────────────────────────────────────────────────┐
│ MODIFYING POLARIZATION OF AT LEAST ONE OF THE ELECTROMAGNETIC       │─228
│ RADIATION BEAM AND A PORTION OF THE ELECTROMAGNETIC RADIATION       │
│ BEAM REFLECTED FROM THE FOCAL POINT LOCATION                        │
└─────────────────────────────────────────────────────────────────────┘
                                  ▼
┌─────────────────────────────────────────────────────────────────────┐
│ USING THE POLARIZATION-SENSITIVE DEVICE TO REFLECT A PORTION OF     │─230
│ THE ELECTROMAGNETIC RADIATION BEAM REFLECTED FROM THE FOCAL POINT   │
│ LOCATION SO AS TO BE INCIDENT UPON THE SENSOR                       │
└─────────────────────────────────────────────────────────────────────┘
```

FIG. 6

CONFOCAL LASER EYE SURGERY SYSTEM

CROSS-REFERENCES TO RELATED APPLICATIONS

This application is a divisional of and claims priority to U.S. patent application Ser. No. 16/188,119, filed Nov. 12, 2018, which claims priority to and is a divisional of U.S. patent application Ser. No. 14/576,593, filed Dec. 19, 2014, now U.S. Pat. No. 10,123,696, which claims priority to and incorporates by reference the entire contents of U.S. Provisional Application No. 61/970,854, filed on Mar. 26, 2014, and U.S. Provisional Application No. 62/043,749, filed on Aug. 29, 2014.

FIELD OF THE INVENTION

The field of the present invention generally relates to laser surgery systems, and more particularly, to systems and methods for imaging and treating the eye.

BACKGROUND OF THE INVENTION

Many patients may have visual errors associated with the refractive properties of the eye such as nearsightedness, farsightedness and astigmatism. Astigmatism may occur when the corneal curvature is unequal in two or more directions. Nearsightedness can occur when light focuses before the retina, and farsightedness can occur with light refracted to a focus behind the retina.

There are numerous prior surgical approaches for reshaping the cornea. Over the years, surgical laser systems have replaced manual surgical tools in ophthalmic procedures. Indeed, with applications in a variety of different procedures, surgical laser systems have become ubiquitous in eye surgery. For instance, in the well-known procedure known as LASIK (laser-assisted in situ keratomileusis), a laser eye surgery system employing ultraviolet radiation is used for ablating and reshaping the anterior surface of the cornea to correct a refractive condition, such as myopia or hyperopia. Prior to ablation during LASIK, another surgical laser system employing a non-ultraviolet, ultra-short pulsed laser beam is used to incise the cornea to create a flap so as to expose an underlying portion of the corneal bed, which is then ablated and reshaped with ultraviolet laser beams from an excimer laser. Afterwards, the treated portion is covered with the corneal flap.

Laser eye surgery systems have also been developed for cataract procedures. These systems can be used for various surgical procedures, including for instance: (1) creating one or more incisions in the cornea, or in the limbus to reshape the cornea, (2) creating one or more incisions in the cornea to provide access for a cataract surgery instrument and/or to provide access for implantation of an intraocular lens, (3) incising the anterior lens capsule (anterior capsulotomy) to provide access for removing a cataractous lens, (4) segmenting and/or fragmenting a cataractous lens, and/or (5) incising the posterior lens capsule (posterior capsulotomy) for various cataract-related procedures.

For example, arcuate incisions are conical incisions made in the cornea. Typically, to prevent an incision from penetrating entirely through the cornea, an arcuate incision is made that does not penetrate the posterior surface of the cornea. Some laser eye surgery systems are capable of making intrastromal arcuate incisions by a laser where the incision is completely contained within the thickness of the cornea and does not penetrate the anterior or posterior surfaces of the cornea.

Typically, some form of imaging is used with laser cataract surgery systems to image and identify one or more surfaces of the eye. In some instances, it may be desirable to accurately identify, detect, and/or image various surfaces of the cornea before, during, or after surgery. For example, in some situations, it may be desirable to accurately determine a thickness of the cornea by imaging and/or by identifying an anterior and a posterior surface of the cornea. However, the cornea's birefringent characteristics may make the identification, detection, and/or imaging of the posterior surface of the corneal more difficult.

In other situations, an image of a proposed laser cut arcuate incision is overlaid on top of an imaged cornea for a surgeon to verify that the proposed incision does not penetrate the posterior surface of the cornea. If the incision is intrastromal, the surgeon also verifies that the proposed incision does not penetrate the anterior surface of the cornea. However, the image provided is typically just a cross-sectional image of the cut overlaid on the cornea, showing only one plane of the proposed incision. While the surgeon can verify that the proposed incision of the displayed cross-sectional plane is correct, he or she cannot verify that the incision is correct over the entire length of the proposed cut. Thus, laser surgery and imaging systems with improved characteristics to allow better imaging, detection, and treatment may be beneficial.

SUMMARY OF THE INVENTION

Accordingly, this disclosure provides imaging systems and related methods that can be used in suitable laser surgery systems, including laser eye surgery systems, so as to obviate one or more problems due to limitations and disadvantages of the related art. In many embodiments, improved methods, devices and systems are provided for imaging the eye and various ocular structures, such as the surfaces of the cornea, the crystalline lens, and so on. For instance, some embodiments provide imaging and identification of the posterior surface of the cornea as well as of the crystalline lens surface. Systems and methods are also provided for imaging ocular structures in a low power imaging mode, and for treating those structures in a high power treatment mode. In other embodiments, systems and methods are provided for imaging a surgical procedure on an ocular structure by previewing an incision over its entire length.

In some embodiments, methods of imaging an eye are provided. These methods may include focusing a first electromagnetic radiation beam to a focal point at a location in the eye, the first electromagnetic radiation beam having a first polarization. The methods may further include focusing a second electromagnetic radiation beam to a focal point at the location in the eye, the second electromagnetic radiation beam having a second polarization which is different from the first polarization. The methods may further include generating a first intensity signal indicative of an intensity of electromagnetic radiation reflected from the eye in response to the step of focusing the first electromagnetic radiation beam, and generating a second intensity signal indicative of an intensity of electromagnetic radiation reflected from the eye in response to the step of focusing the second electromagnetic radiation beam. One or more images of the eye may then be generated with the first and second intensity signals and utilized for treatment planning.

Optionally, the first and second electromagnetic radiation beams may be focused using a beam scanner. The methods may further include scanning the focal point of the first electromagnetic radiation beam to a plurality of different locations in a first region of the eye, and scanning the focal point of the second electromagnetic radiation beam to a plurality of different locations in a second region of the eye. A first intensity profile may be generated that is indicative of intensities of electromagnetic radiation reflected from the eye in response to the step of scanning the focal point of the first electromagnetic radiation beam. A second intensity profile may be generated that is indicative of intensities of electromagnetic radiation reflected from the eye in response to the step of scanning the focal point of the second electromagnetic radiation beam. In some embodiments, one image of the eye is generated per the first and second intensity profiles. A beam scanner may include an XY-scan device that is configured to deflect the first and second electromagnetic radiation beams in two dimensions transverse to a propagation of first and second electromagnetic radiation beams. The focal point of the first and second electromagnetic radiation beam may be scanned in the two dimensions using the XY-scan device according to some embodiments, and may thereby provide an image of the eye with at least two dimensions.

Optionally, the beam scanner may further include a Z-scan device that is configured to vary a convergence depth of the beam within the eye. In some embodiments, the Z-scan device may vary a convergence angle of the beam. The focal point of the first and second electromagnetic radiation beam may then be scanned in the three dimensions using the XY-scan device and the Z-scan device. Accordingly, the image of the eye may be three-dimensional according to some embodiments.

In some embodiments, the first and second intensity signals may be generated by a sensor. The sensor may be a confocal sensor. The methods may further include the step of blocking reflected electromagnetic radiation from reaching the sensor, where the electromagnetic radiation has reflected from eye locations other than the location of the focal point of the first and second electromagnetic radiation beams.

In some methods, the first electromagnetic radiation beam may be generated by passing an electromagnetic radiation beam through a wave plate in a first position so as to polarize the electromagnetic radiation beam with the first polarization. The wave plate may be rotated by an angle to a second position. The second electromagnetic radiation beam may be generated by passing the electromagnetic radiation beam through the wave plate in the second position.

Optionally, the wave plate may be a one-quarter wave plate. In some embodiments, the wave plate may be rotated by an acute angle for generating the second electromagnetic radiation beam. In some embodiments, the wave plate may be rotated ninety degrees for generating the second electromagnetic radiation beam. In some embodiments, the first and second electromagnetic radiation beams may be polarized with the first and second polarizations by using a Faraday rotator, or a rotating beam-splitter.

In some embodiments, the method may include the step of passing electromagnetic radiation reflected from the eye in response to the step of focusing the first electromagnetic radiation beam through the wave plate in the first position. Further, electromagnetic radiation reflected from the eye in response to the step of focusing the second electromagnetic radiation beam may be passed through the wave plate in the second position.

In additional embodiments, methods of imaging an eye are provided, where the method includes scanning a focal point of a first electromagnetic radiation beam to a plurality of locations in the eye, where the first electromagnetic radiation beam has a first polarization. The methods may further include scanning a focal point of a second electromagnetic radiation beam to at least a portion of the plurality of locations in the eye, where the second electromagnetic radiation beam has a second polarization different than the first polarization. A first intensity profile indicative of an intensity of electromagnetic radiation reflected from the eye may be generated in response to the step of scanning the first electromagnetic radiation beam. And, a second intensity profile indicative of an intensity of electromagnetic radiation reflected from the eye may be generated in response to the step of scanning the second electromagnetic radiation beam. An image of the eye may be produced using the first and second intensity profiles.

Optionally, the method may include receiving a plurality of parameters corresponding to the treatment planning, generating a three-dimensional representation of the treatment planning, mapping the three-dimensional representation onto the image of the eye, and displaying the mapped image for the treatment planning. The treatment planning may include an arcuate incision. The system can verify that the arcuate incision lies within the cornea. The received parameters may include a treatment axis and a treatment length transverse to the axis. The image of the eye may be in a plane of the treatment axis and the treatment length. In some embodiments, the three-dimensional representation is mapped onto the image of the eye by projecting the three-dimensional representation onto a two-dimensional space. The displayed image may include a cornea of the eye including an anterior and posterior region. The anterior and posterior of the cornea are optionally highlighted. The treatment planning may also include one of a primary incision and a side-port incision.

In some embodiments, the methods may be for imaging a cornea of the eye, where the cornea has an anterior surface and a posterior surface. The anterior surface of the cornea may be identified using the first intensity profile, and the posterior surface of the cornea may be identified using at least a portion of the second intensity profile.

In some embodiments, methods of imaging a cornea may include the step of generating a first electromagnetic radiation beam using a beam source and passing the first electromagnetic radiation beam through a wave plate. The first electromagnetic radiation beam may be propagated to a beam scanner. The first electromagnetic radiation beam may be focused to a focal point at a location in the cornea of the eye using the beam scanner. A first reflected electromagnetic radiation from the focal point may be received after focusing the first electromagnetic radiation beam. The first received electromagnetic radiation may be directed through the wave plate and towards a sensor. A first intensity signal may be generated that is indicative of an intensity of the first received electromagnetic radiation. Thereafter, the wave plate may be rotated at an angle after generating the first intensity signal. A second electromagnetic radiation beam may be passed through the rotated wave plate and focused to a focal point at the location in the cornea of the eye. A second reflected electromagnetic radiation from the focal point may be received in response to the step of focusing the second electromagnetic radiation beam. The second received electromagnetic radiation may be directed through the rotated wave plate and toward the sensor. A second intensity signal may be generated that is indicative of an intensity of the second received electromagnetic radiation. The anterior surface of the cornea may be identified using the first intensity signal and at least some portions of the posterior surface of the cornea may be identified using the second intensity signal.

In some embodiments, the method may include the steps of generating an image of the eye using the identified anterior surface and posterior surface of the cornea, receiving a plurality of parameters corresponding to a treatment plan, generating a three-dimensional representation of the treatment plan, mapping the three-dimensional representation onto the image of the eye, and displaying the mapped image for verification.

Optionally, the treatment plan may include an arcuate incision. The arcuate incision may be verified to lie within the cornea. The received parameters may include a treatment axis and a treatment length transverse to the axis. The image of the eye may be in a plane of the treatment axis and the treatment length. In some embodiments, the three-dimensional representation is mapped onto the image of the eye by projecting the three-dimensional representation onto a two-dimensional space. The anterior surface and posterior surface of the cornea may be highlighted. Alternatively, the treatment plan includes one of a primary and side-port incision.

Certain aspects of the present invention provide methods of imaging a cornea, where the cornea has a first region with a first birefringence and a second region with a second birefringence. The methods may include a step of directing a first electromagnetic radiation beam through the first region of the cornea to a first location in the eye, where the first electromagnetic radiation beam may have a first polarization. A second electromagnetic radiation beam may be directed through the second region of the cornea to a second location in the eye, where the second electromagnetic radiation beam may have a second polarization different from the first polarization. An image of the eye may be generated that encompasses the first and second locations using electromagnetic radiation signals reflected from the eye in response to the steps of directing the first and second electromagnetic radiation beams.

In still other aspects of the present invention, where methods of imaging an eye are provided, the methods may include the step of generating an electromagnetic radiation beam using a beam source. The electromagnetic radiation beam may be elliptically polarized, and may be focused to a focal point in the eye. Further, the focal point of the elliptically polarized electromagnetic radiation beam may be scanned to a plurality of different locations in the eye. Electromagnetic radiation reflected from the focal point may be received in response to the step of scanning the elliptically polarized electromagnetic radiation. This received reflected electromagnetic radiation may be directed toward a sensor, and an intensity profile may be generated that is indicative of an intensity of the received reflected electromagnetic radiation. A first surface and a second surface of the eye may be identified using the intensity profile.

In some embodiments, the methods may further include the step of passing the reflected electromagnetic radiation through an aperture to block reflected electromagnetic radiation from eye locations other than the location of the focal point of the elliptically polarized electromagnetic radiation beam.

In some embodiments, the methods may further include the step of generating an image of the eye using the identified first surface and second surface of the cornea, receiving a plurality of parameters corresponding to a treatment plan, generating a three-dimensional representation of the treatment plan, mapping the three-dimensional representation onto the image of the eye, and displaying the mapped image for verification. The treatment plan may include an arcuate incision. The arcuate incision may be verified to lie within the cornea. The received parameters may include a treatment axis and a treatment length transverse to the axis. The image of the eye may be in some embodiments in a plane of the treatment axis and the treatment length. The three-dimensional representation may be mapped onto the image of the eye by projecting the three-dimensional representation onto a two-dimensional space. The first surface and second surface of the cornea are optionally highlighted. Alternatively, the treatment plan comprises one of a primary and side-port incision.

In other embodiments, systems for imaging an eye are provided, wherein the systems may include a laser beam source configured to output a beam along a beam path toward the eye. A beam scanner may be included to focus the outputted beam to a focal point at a location in the eye. The systems may include a variable axis polarization system positioned along the beam path between the laser beam source and the eye. The polarization system may be configured to polarize an outputted beam with a first polarization or a second polarization. The polarization system may polarize an outputted beam with the first polarization when in a first configuration, and may polarize the outputted beam with the second polarization when in a second configuration. The system may further include a sensor positioned to receive reflected electromagnetic radiation from the eye.

In some embodiments, the wave plate may be further positioned and configured to receive reflected electromagnetic radiation from the focal point before the reflected electromagnetic radiation reaches the sensor. Optionally, the systems may further include a polarizing beam-splitter positioned to direct the reflected electromagnetic radiation that passed through the wave plate to the sensor. An aperture may be positioned to block reflected electromagnetic radiation from eye locations other than the location of the focal point of the outputted beam. The wave plate may be a one-quarter wave plate.

In some aspects, the wave plate may be rotatable between the first position and the second position. The wave plate may rotate forty-five degrees between the first position and the second position. Optionally, the wave plate may rotate ninety degrees between the first position and the second position. The beam scanner may include an XY-scan device and a Z-scan device. The XY-scan device may be configured to deflect the outputted beam in two dimensions transverse to a propagation of outputted beam, while the Z-scan device may be configured to vary a convergence depth of the beam.

In some embodiments, the systems may include a processor generating an image of the eye using an output of the sensor. A user interface device receiving a plurality of parameters corresponding to a treatment plan. The processor may generate a three-dimensional representation of the treatment plan and map the three-dimensional representation onto the image of the eye. A display system displays the mapped image for verification. The treatment planning may include an arcuate incision. The processor may verify that the arcuate incision lies within the cornea. The parameters may include a treatment axis and a treatment length transverse to the axis. The image of the eye may be in a plane of the treatment axis and the treatment length. In some embodiments, the three-dimensional representation may be mapped onto the image of the eye by projecting the three-dimensional representation onto a two-dimensional space. The displayed image may include a cornea of the eye including an anterior and posterior. The anterior and posterior of the cornea are optionally highlighted. Alternatively, the treatment planning comprises one of a primary and side-port incision.

Certain aspects of the invention disclose systems for imaging an eye using elliptically polarized light. The system may include a laser beam source configured to output a beam along a beam path toward the eye. A wave plate may be positioned along the beam path between the laser beam source and the eye and may be configured to elliptically polarize an outputted beam. A beam scanner may be configured to focus the elliptically polarized outputted beam to a focal point at a location in the eye. A sensor may be positioned to receive reflected electromagnetic radiation from the focal point. Further, an aperture may be positioned to block reflected electromagnetic radiation from eye locations other than the location of the focal point of the outputted beam.

In some embodiments, the systems may further include a processor generating an image of the eye using an output of the sensor, a user interface device receiving a plurality of parameters corresponding to a treatment plan. The processor may generate a three-dimensional representation of the treatment plan, and map the three-dimensional representation onto the image of the eye. A display system displays the mapped image for verification. The treatment planning may include an arcuate incision.

In another embodiment, a laser-based eye surgery system for treating and imaging an eye may include a laser delivery system for delivering an electromagnetic radiation beam to a target in the eye, an attenuator for polarizing the electromagnetic radiation beam, a shutter for allowing or blocking the electromagnetic radiation beam, a beam-splitter for separating the electromagnetic radiation beam, where the beam-splitter may be substantially non-polarizing for reflecting a returning confocal beam. A bypass assembly for directing the electromagnetic radiation beam and a sensor for imaging the eye may be included.

In many of the embodiments, the electromagnetic radiation beam may be directed to bypass the non-polarized beam-splitter in a treatment mode. The electromagnetic radiation beam may be directed toward the non-polarized beam-splitter while bypassing the bypass assembly in an imaging mode. The bypass assembly may include one or more mirrors or prisms. The electromagnetic radiation beam when bypassing the non-polarized beam-splitter provides a high power level for treatment. The electromagnetic radiation beam when directed toward the non-polarized beam-splitter provides a low power level for imaging.

In many embodiments of the system, the system includes a processor generating an image of the eye using an output of the sensor and a user interface device receiving a plurality of parameters corresponding to a treatment plan. The processor generates a three-dimensional representation of the treatment plan, and maps the three-dimensional representation onto the image of the eye. A display system displays the mapped image for verification. The treatment planning may include an arcuate incision.

In another embodiment, a method for treating and imaging an eye using a laser-based eye surgery system includes the steps of generating an electromagnetic radiation beam, delivering the electromagnetic radiation beam to a target in the eye, directing the electromagnetic radiation beam to a bypass assembly for treatment, and directing the electromagnetic radiation beam toward a beam-splitter for imaging. The beam-splitter may be substantially non-polarizing for reflecting a returning confocal beam. The step of directing the electromagnetic radiation beam to a bypass assembly further may provide a high power level for treatment. The step of directing the electromagnetic radiation beam toward a beam-splitter further may provide a low power level for imaging.

Some embodiments of the method for treating and imaging an eye may include the steps of generating an image of the eye in response to the step of directing the electromagnetic radiation beam in the low power level for imaging, receiving a plurality of parameters corresponding to treatment planning, generating a three-dimensional representation of the treatment planning, mapping the three-dimensional representation onto the image of the eye, and displaying the mapped image for the treatment planning. The treatment planning may include an arcuate incision.

Another embodiment provides a method of reversibly bypassing an imaging assembly in an optical path of a laser surgical system. The method includes using a beam source to generate an electromagnetic beam. The electromagnetic beam is propagated from the beam source to a scanner along an optical path that includes a first optical element associated with a confocal detection assembly. The electromagnetic beam is focused to a focal point at a location within the eye, and a scanner scans the focal point to different locations within the eye. A portion of the electromagnetic beam is reflected from the focal point location back along the optical path to the first optical element, which diverts a portion of the reflected electromagnetic radiation to a sensor. The sensor generates an intensity signal indicative of the intensity of a portion of the electromagnetic beam reflected from the focal point location and propagated to the sensor via the first optical element. The method includes reversibly diverting the electromagnetic beam along a diversion optical path around the first optical element, and preferably, the beam direction and position are substantially the same at the entry of and exit from the diversion optical path in a direction transverse to the direction of propagation of the electromagnetic beam.

The first optical element is preferably a beam-splitter that directs a portion of the reflected electromagnetic radiation to the sensor. The beam-splitter is preferably stationary. In one embodiment, the beam-splitter is not a polarizing beam-splitter, i.e., its ability to split a beam is not based on a polarization property of the reflected light.

In many embodiments of the method, the electromagnetic beam can be configured along the optical path so as to not modify tissue. For example, the electromagnetic beam can have an energy level below a threshold level for tissue modification. Alternatively, the electromagnetic beam can be configured at an energy level designed to modify tissue.

The electromagnetic beam can have any suitable configuration. For example, the electromagnetic beam can include a plurality of laser pulses having a wavelength between 320 nanometers and 430 nanometers. As another example, the electromagnetic beam can include a plurality of laser pulses having a wavelength between 800 nanometers and 1100 nanometers.

In another embodiment, a laser eye surgery system is provided. The system includes a light source, an eye interface device, a scanning assembly, a confocal detection assembly and a confocal bypass assembly. The light source is configured to generate an electromagnetic beam. The scanning assembly is operable to scan a focal point of an electromagnetic beam to different locations within the eye. The eye interface device is configured to interface with an eye of a patient. An optical path is configured to propagate the electromagnetic beam from a light source to the focal point, and also configured to propagate a portion of the electromagnetic beam reflected back from the focal point location along at least a portion of the optical path. The optical path comprises a first optical element associated with a confocal detection assembly that diverts a portion of the reflected electromagnetic radiation to a sensor. A confocal detection assembly is configured to generate an intensity signal indicative of intensity of a portion of the electromagnetic beam reflected from the focal point location. The confocal bypass assembly is configured to reversibly divert the electromagnetic beam along a diversion optical path around the first optical element. Preferably, the beam position is substantially the same at the entry of, and at the exit from the diversion optical path in a direction transverse to the direction of propagation of the electromagnetic beam. Further, the propagation direction is the same at the entry and the exit of the diversion optical path.

The scanning assembly comprises a Z-scan device operable to vary the location of the focal point in the direction of propagation of the electromagnetic beam, and an XY-scan device operable to vary the location of the focal point transverse to the direction of propagation of the electromagnetic beam.

The detection assembly preferably comprises an aperture configured to block portions of the electromagnetic beam reflected from locations other than the focal point from reaching the sensor.

The first optical element is generally associated with a confocal imaging assembly, and is preferably a beam-splitter that directs a portion of the reflected electromagnetic radiation to the sensor. The beam-splitter is preferably stationary. In one embodiment, the beam-splitter is not a polarizing beam-splitter, i.e., its ability to split a beam is not based on a polarization property of the reflected light.

In one embodiment, the confocal bypass assembly comprises a bypass prism. The confocal bypass assembly reversibly moves the bypass prism into and out of the optical path, thereby diverting the electromagnetic beam along a diversion optical path around an optical element of a confocal detection assembly operably to divert a portion of the electromagnetic beam to a sensor. In a preferred embodiment, the diversion optical path diverts the electromagnetic beam only around the optical element. In one embodiment, the confocal bypass prism diverts the electromagnetic beam around only the optical element that directs a portion of the reflected electromagnetic radiation to the sensor.

In another embodiment, the laser eye surgery system may include a laser delivery system for delivering an electromagnetic radiation beam to a target in an eye, a beam expander coupled to the laser delivery system for adjusting the diameter of the electromagnetic radiation beam, an attenuator coupled to the expander for polarizing the electromagnetic radiation beam, a shutter coupled to the attenuator for allowing or blocking the electromagnetic radiation beam, and a sensor. A bypass assembly is coupled to the shutter for propagating the electromagnetic radiation beam to bypass a non-polarized beam-splitter and dump in a treatment mode, and for directing the electromagnetic radiation beam toward the non-polarized beam-splitter and dump in an imaging mode while bypassing the bypass assembly. In another embodiment, the eye surgery system delivers the electromagnetic radiation beam in a high power level for treatment, and a low power level for imaging.

In many embodiments, the bypass assembly includes one or more mirrors or prisms. One or more wave plates may be provided to enable confocal imaging of the target in the eye. One or more wave plate angles for imaging ocular structures of the target in the eye may compensate for birefringence effects in the imaged structures.

Optionally, the system may include a processor generating an image of the eye using an output of the sensor and a user interface device receiving a plurality of parameters corresponding to a treatment plan. The processor may generate a three-dimensional representation of the treatment plan and map the three-dimensional representation onto the image of the eye. A display system may display the mapped image for verification. The treatment planning may include an arcuate incision.

In still other aspects of the present invention, where methods of imaging an eye are provided, the methods may include the step of focusing a first electromagnetic radiation beam to a focal point at a location in the eye and focusing a second electromagnetic radiation beam to a focal point at the location in the eye. A first intensity signal is generated indicative of an intensity of electromagnetic radiation reflected from the eye in response to the step of focusing the first electromagnetic radiation beam. A second intensity signal is generated indicative of an intensity of electromagnetic radiation reflected from the eye in response to the step of focusing the second electromagnetic radiation beam. One or more images of the eye are generated with the first and second intensity signals for treatment planning. A plurality of parameters is received corresponding to the treatment planning. A three-dimensional representation of the treatment planning is generated. The three-dimensional representation is mapped onto the image of the eye. The mapped image is displayed for the treatment planning.

In another embodiment, a laser surgery system includes a laser beam source configured to output a beam along a beam path toward the eye. A beam scanner is configured to direct the outputted beam to a plurality of locations in the eye. A sensor is positioned to receive reflected electromagnetic radiation from the eye. A processor is configured to generate one or more images of the eye with the first and second intensity signals for treatment planning. A user input device is configured to receive a plurality of parameters corresponding to the treatment planning. The processor generates a three-dimensional representation of the treatment planning, maps the three-dimensional representation onto the image of the eye. A display is configured to display the mapped image for the treatment planning.

This summary and the following description are merely exemplary, illustrative, and explanatory, and are not intended to limit, but to provide further explanation of the invention as claimed. Additional features, aspects, objects and advantages of embodiments of this invention are set forth in the descriptions, drawings, and the claims, and in part, will be apparent from the drawings and detailed description, or may be learned by practice. The claims are incorporated by reference.

BRIEF DESCRIPTION OF THE DRAWINGS

The novel features of the invention are set forth with particularity in the appended claims. A better understanding of the features and advantages of the present invention will be obtained by referring to the following detailed description that sets forth illustrative embodiments using principles of the invention, as well as to the accompanying drawings of which:

FIGS. 4, 5, and 6 are simplified processes that can be accomplished as part of the process of FIG. 3 according to an embodiment of the invention.

FIG. 10A is a schematic diagram illustrating an embodiment in which a confocal bypass assembly is not placed in the optical path of the electromagnetic beam. FIG. 10B is a schematic diagram illustrating an embodiment in which a confocal bypass assembly is placed in the optical path of the electromagnetic beam.

DETAILED DESCRIPTION OF THE INVENTION

The following description describes various embodiments of the present invention. For purposes of explanation, specific configurations and details are set forth so as to provide a thorough understanding of the embodiments. It will also, however, be apparent to one skilled in the art that embodiments of the present invention can be practiced without certain specific details. Further, to avoid obscuring the embodiment being described, various well-known features may be omitted or simplified in the description.

As used herein, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

Systems for imaging and/or treating a patient's eye are provided. In many embodiments, a free-floating mechanism provides a variable optical path by which a portion of an electromagnetic beam reflected from a focal point disposed within the eye is directed to a path length insensitive imaging assembly, such as a confocal detection assembly. In many embodiments, the free-floating mechanism is configured to accommodate movement of the patient while maintaining alignment between an electromagnetic radiation beam and the patient. The electromagnetic radiation beam can be configured for imaging the eye, can be configured for treating the eye, and can be configured for imaging and treating the eye.

Figure 1:
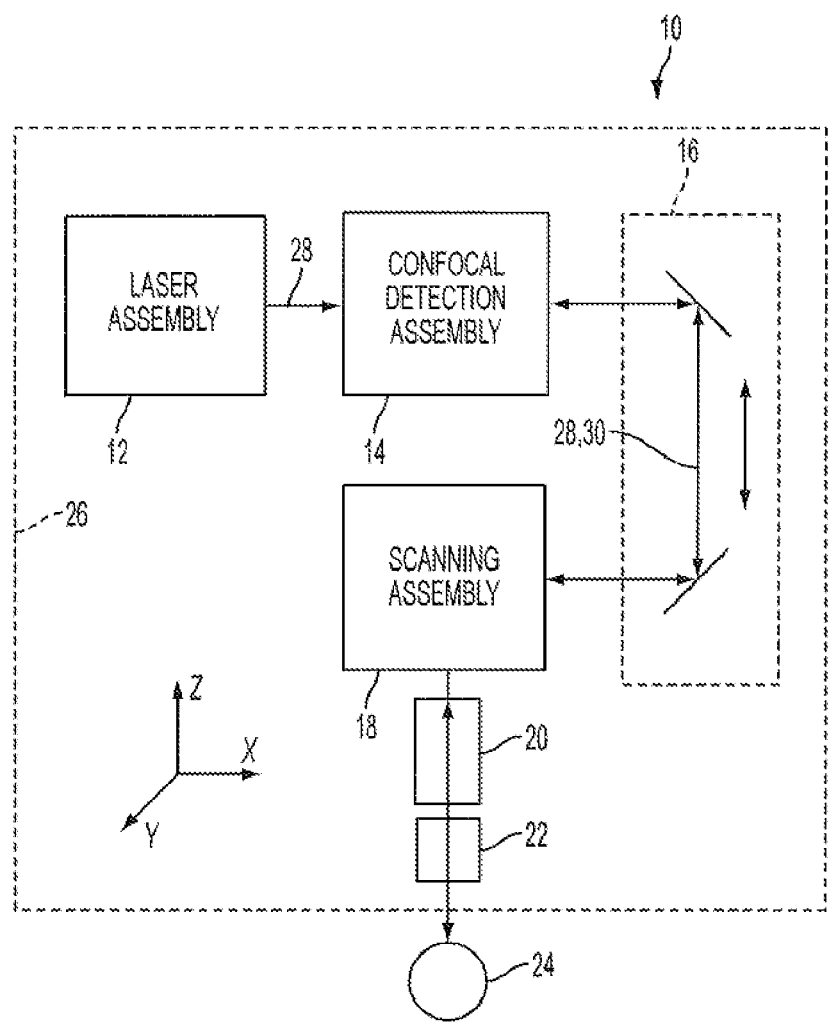
FIG. 1 is a schematic diagram of a laser surgery system according to an embodiment of the invention.

FIG. 1 schematically illustrates a laser surgery system 10 according to many embodiments. The laser surgery system 10 may include a laser assembly 12, a confocal detection assembly 14, a free-floating mechanism 16, a scanning assembly 18, an objective lens assembly 20, and a patient interface device 22. The patient interface device 22 may be configured to interface with a patient 24. The patient interface device 22 may be supported by the objective lens assembly 20, which may be supported by the scanning assembly 18, which may be supported by the free-floating mechanism 16. The free-floating mechanism 16 may have a portion having a fixed position and orientation relative to the laser assembly 12 and the confocal detection assembly 14.

In some embodiments, the patient interface device 22 can be configured to be coupled to an eye of the patient 24 using a vacuum as described in co-pending U.S. patent application Ser. No. 14/068,994, entitled "Liquid Optical Interface for Laser Eye Surgery System," filed Oct. 31, 2013, the entire disclosure of which is incorporated herein by reference. The laser surgery system 10 can further optionally include a base assembly 26 that can be fixed in place or be repositionable. For example, the base assembly 26 can be supported by a support linkage that is configured to allow selective repositioning of the base assembly 26 relative to a patient, and/or to allow securing the base assembly 26 in a selected fixed position relative to the patient. Such a support linkage can be a fixed support base, or a movable cart that can be repositioned to a suitable location adjacent to a patient. In many embodiments, the support linkage includes setup joints with each setup joint being configured to permit selective articulation of the setup joint, and can be selectively locked to prevent inadvertent articulation of the setup joint, thereby securing the base assembly 26 in a selected fixed position relative to the patient when the setup joints are locked.

In many embodiments, the laser assembly 12 may be configured to emit an electromagnetic radiation beam 28. The beam 28 can include a series of laser pulses of any suitable energy level, duration, and repetition rate.

In many embodiments, the laser assembly 12 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required to image and/or to modify an intraocular target as compared to laser pulses having longer durations.

The laser assembly 12 may produce laser pulses having a wavelength suitable to treat and/or to image tissue. For example, the laser assembly 12 can be configured to emit an electromagnetic radiation beam 28 such as that emitted by any of the laser surgery systems described in co-pending U.S. patent application Ser. No. 14/069,044, entitled "Laser Eye Surgery System," filed Oct. 31, 2013, and U.S. patent application Ser. No. 12/987,069, entitled "Method and System For Modifying Eye Tissue and Intraocular Lenses," filed Jan. 7, 2011, the full disclosures of which are incorporated herein by reference. In an embodiment, the laser assembly 12 may produce laser pulses having a wavelength in the range of 1020 nm to 1050 nm. In another embodiment, the laser assembly 12 may have a diode-pumped solid-state configuration with a 1030 (+/−5) nm center wavelength. In yet another embodiment, the laser assembly 12 may produce laser pulses having a wavelength 320 nm to 430 nm. For example, the laser assembly 12 may include an Nd:YAG laser source operating at the 3rd harmonic wavelength (355 nm), and producing pulses having pulse durations in the range of 50 picoseconds to 15 nanoseconds. Depending on the spot size, the typical pulse energies can be in the nano Joule to micro Joule range. The laser assembly 12 can also include two or more lasers of any suitable configuration.

The laser assembly 12 may include control and conditioning components. In an embodiment, the control components may include a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. The conditioning components may include an adjustable zoom assembly and a fixed optical relay to transfer the laser pulses over a distance while accommodating laser pulse beam positional and/or directional variability, thereby providing increased tolerance for component variation.

In many embodiments, the laser assembly 12 and the confocal detection assembly 14 may have fixed positions relative to the base assembly 26. The beam 28 emitted by the laser assembly 12 may propagate along a fixed optical path through the confocal detection assembly 14 to the free-floating mechanism 16. The beam 28 may propagate through the free-floating mechanism 16 along a variable optical path 30, which may deliver the beam 28 to the scanning assembly 18. In many embodiments, the beam 28 emitted by the laser assembly 12 may be collimated so that the beam 28 is not impacted by patient movement-induced changes in the length of the optical path between the laser assembly 12 and the scanner 16. The scanning assembly 18 may be operable to scan the beam 28 (e.g., via controlled variable deflection of the beam 28) in at least one dimension. In many embodiments, the scanning assembly 18 is operable to scan the beam 28 in two dimensions transverse to the direction of propagation of the beam 28, and may be further operable to scan the location of a focal point of the beam 28 in the direction of propagation of the beam 28. The scanned beam may be emitted from the scanning assembly 18 to propagate through the objective lens assembly 20, through the interface device 22, and to the patient 24.

The free-floating mechanism 16 may be configured to accommodate a range of movement of the patient 24 relative to the laser assembly 12 and the confocal detection assembly 14 in one or more directions while maintaining alignment of the beam 28 emitted by the scanning assembly 18 with the patient 24. For example, the free-floating mechanism 16 may be configured to accommodate a range movement of the patient 24 in any direction defined by any combination of unit orthogonal directions (X, Y, and Z).

Because the patient interface device 22 may be interfaced with the patient 24, movement of the patient 24 may result in corresponding movement of the patient interface device 22, the objective lens assembly 20, and the scanning assembly 18. The free-floating mechanism 16 can include, for example, any suitable combination of a linkage that accommodates relative movement between the scanning assembly 18 and, for example, the confocal detection assembly 14, and optical components suitably coupled to the linkage so as to form the variable optical path 30. In an embodiment, the free-floating mechanism 16 can be configured as described in U.S. patent application Ser. No. 14/191,095 and PCT Application No. PCT/US2014/018752, filed Feb. 26, 2014 and entitled "Laser Surgery System," the entire disclosures of which are incorporated herein by reference.

A portion of electromagnetic radiation beam 28 may reflect from an eye tissue at the focal point, and may propagate back to the confocal detection assembly 14. Specifically, a reflected portion of the electromagnetic radiation beam 28 may travel back through the patient interface device 22, back through the objective lens assembly 20, back through (and de-scanned by) the scanning assembly 18, back through the free-floating mechanism 16 (along the variable optical path 30), and to the confocal detection assembly 14. In many embodiments, the reflected portion of the electromagnetic radiation beam that travels back to the confocal detection assembly 14 may be directed so it is incident upon a sensor that generates an intensity signal indicative of the intensity of the incident portion of the electromagnetic radiation beam. Coupled with associated scanning of the focal point within the eye, the intensity signal can be processed in conjunction with the parameters of the scanning to image/locate structures of the eye, such as the anterior surface of the cornea, the posterior surface of the cornea, the iris, the anterior surface of the lens capsule, the posterior surface of the lens capsule, and so on. In many embodiments, the amount of the reflected electromagnetic radiation beam that travels to the confocal detection assembly 14 may be substantially independent of expected variations in the length of the variable optical path 30 due to patient movement, thereby enabling the ability to ignore patient movements when processing the intensity signal to image/locate structures of the eye.

The locations of the one or more optical structures of the eye can be determined from the measurements obtained as discussed herein. The image of the eye may comprise a sagittal view of the eye, a transverse view of the eye, or an anterior view of the eye, and combinations thereof. The one or more images of the eye may comprise a tomography image showing a plane of the eye and an anterior camera view of the eye, and the one or more optical structures can be placed on the one or more images to provide one or more reference locations to the user. In many embodiments, the one or more images comprise real time images provided for the user to plan and verify eye incisions.

The optical structure of the eye may comprise one or more structures of the eye related to optics of the eye, and the tissue structure of the eye may comprise one or more tissues of the eye. The optical structure of the eye may comprise one or more of an optical axis of the eye, a visual axis of the eye, a line of sight of the eye, a pupillary axis of the eye, a fixation axis of the eye, a vertex of the cornea, an anterior nodal point of the eye, a posterior nodal point of the eye, an anterior principal point of the eye, a posterior principal point of the eye, a keratometry axis, a center of curvature of the anterior corneal surface, a center of curvature of the posterior corneal surface, a center of curvature of the anterior lens capsule, a center of curvature of the posterior lens capsule, a center of the pupil, a center of the iris, a center of the entrance pupil, or a center of the exit pupil of the eye. The one or more tissue structures may comprise one or more of the iris, a plane of the iris, an outer boundary of the iris, the limbus, a center of the limbus, scleral blood vessels, a center of the cornea, a thickness profile of the cornea, a center of curvature of a thickness profile of the cornea, a tissue stained with a dye such as an ink, the vertex of the cornea, the optical axis of the eye, a center of curvature of the anterior surface of the cornea, a center of curvature of the anterior lens capsule, and a center of curvature of the posterior lens capsule.

Some embodiments provide methods of imaging a cornea or a lens of an eye using the laser surgery system 10. The methods may include the step of generating a first electromagnetic radiation beam using a beam source and passing the first electromagnetic radiation beam through a wave plate. The first electromagnetic radiation beam may be propagated to a beam scanner. The first electromagnetic radiation beam may be focused to a focal point at a location in the cornea of the eye using the beam scanner. A first reflected electromagnetic radiation from the focal point may be received after focusing the first electromagnetic radiation beam. The first received electromagnetic radiation may be directed through the wave plate and towards a sensor. A first intensity signal may be generated that is indicative of an intensity of the first received electromagnetic radiation. Thereafter, the wave plate may be rotated at an angle after generating the first intensity signal. A second electromagnetic radiation beam may be passed through the rotated wave plate and focused to a focal point at the location in the cornea of the eye. A second reflected electromagnetic radiation from the focal point may be received in response to the step of focusing the second electromagnetic radiation beam. The second received electromagnetic radiation may be directed through the rotated wave plate and toward the sensor. A second intensity signal may be generated that is indicative of an intensity of the second received electromagnetic radiation. The anterior surface of the cornea may be identified using the first intensity signal and at least some portions of the posterior surface of the cornea may be identified using the second intensity signal. A similar approach utilizing multiple wave plate angles is used for imaging the anterior surface of the lens with high contrast.

The laser surgery system 10 may include a variable axis polarization system positioned along the beam path between the laser beam source and the eye. The polarization system may be configured to polarize an outputted beam with a first polarization state or a second polarization state. The polarization system may set the polarization state of an outputted beam when in a first configuration, and may set another polarization state when in a second configuration.

In some embodiments, the wave plate may be further positioned and configured to receive reflected electromagnetic radiation from the focal point before the reflected electromagnetic radiation reaches the sensor. Optionally, the laser surgery system 10 may further include a polarizing beam-splitter positioned to direct the reflected electromagnetic radiation that passed through the wave plate to the sensor. An aperture may be positioned to block reflected electromagnetic radiation from eye locations other than the location of the focal point of the outputted beam.

In some embodiments, the wave plate may be rotatable between the first position and the second position. The wave plate may rotate forty-five degrees between the first position and the second position. Optionally, the wave plate may rotate ninety degrees between the first position and the second position. The beam scanner may include an XY-scan device and a Z-scan device. The XY-scan device may be configured to deflect the outputted beam in two dimensions transverse to a propagation of outputted beam. The Z-scan device may be configured to vary a convergence angle of the beam.

Figure 2:
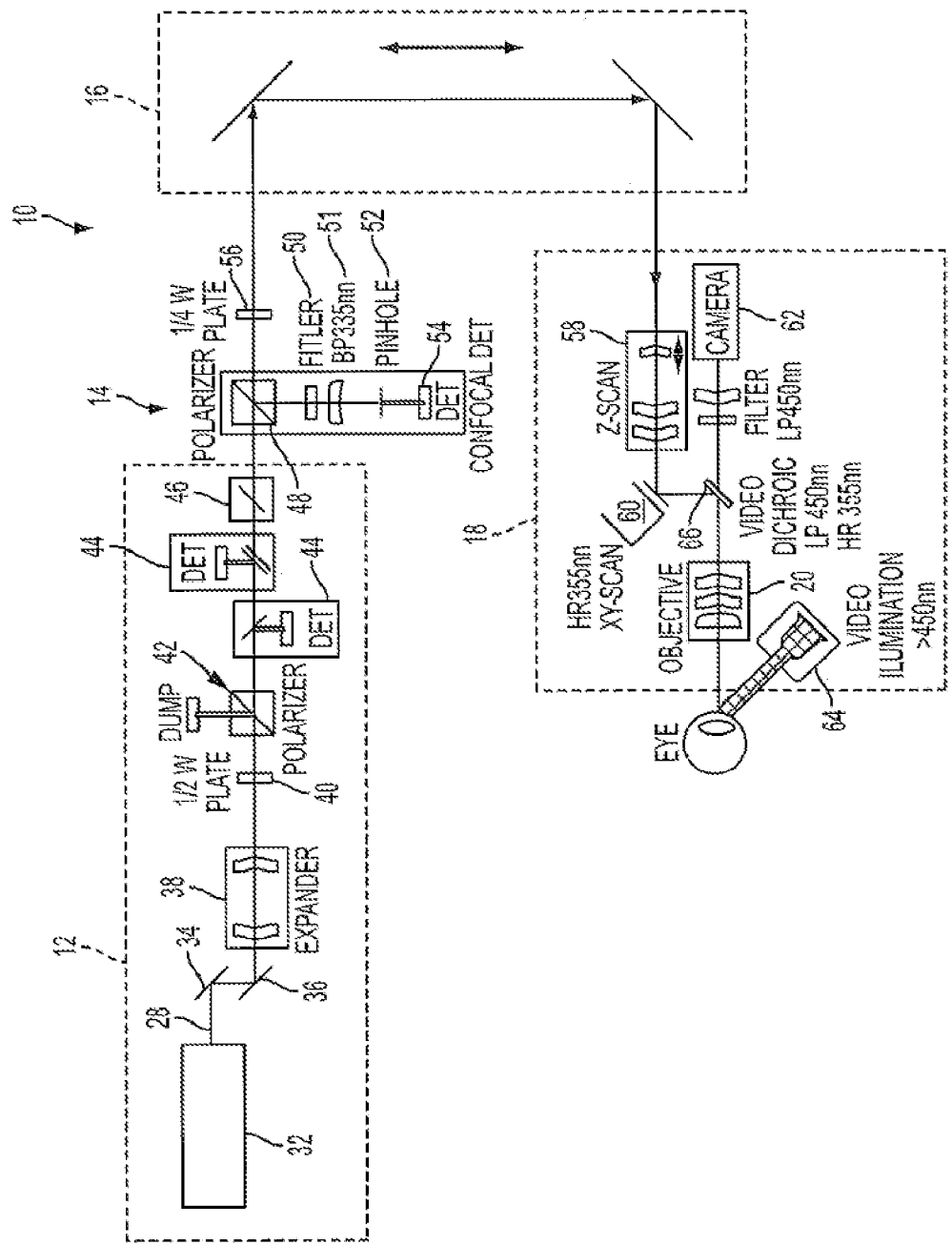
FIG. 2 is a schematic diagram of the laser surgery system of FIG. 1 according to an embodiment of the invention.

FIG. 2 schematically illustrates details of an embodiment of the laser surgery system 10. Specifically, example configurations are schematically illustrated for the laser assembly 12, the confocal detection assembly 14, and the scanning assembly 18. As shown in the illustrated embodiment, the laser assembly 12 may include an ultrafast (UF) laser 32 (e.g., a femtosecond laser), alignment mirrors 34, 36, a beam expander 38, a one-half wave plate 40, a polarizer and beam dump device 42, output pickoffs and monitors 44, and a system-controlled shutter 46. The electromagnetic radiation beam 28 output by the laser 32 may be deflected by the alignment mirrors 34, 36. In many embodiments, the alignment mirrors 34, 36 may be adjustable in position and/or orientation so as to provide the ability to align the beam 28 with the downstream optical path through the downstream optical components. Next, the beam 28 may pass through the beam expander 38, which can increase the diameter of the beam 28. The expanded beam 28 may then pass through the one-half wave plate 40 before passing through the polarizer 42. The beam exiting the polarizer 42 may be linearly polarized. The one-half wave plate 40 can rotate this polarization. The amount of light passing through the polarizer 42 depends on the angle of the rotation of the linear polarization. Therefore, the one-half wave plate 40 with the polarizer 42 may act as an attenuator of the beam 28. The light rejected from this attenuation may be directed into the beam dump. Next, the attenuated beam 28 may pass through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

As shown in the illustrated embodiment, the confocal detection assembly 14 can include a polarization-sensitive device such as a polarized or a non-polarized beam-splitter 48, a filter 50, a focusing lens 51, a pinhole aperture 52, and a detection sensor 54. A one-quarter wave plate 56 may be disposed downstream of the polarized beam-splitter 48. The beam 28 as received from the laser assembly 12 may be polarized so as to pass through the polarized beam-splitter 48. Next, the beam 28 may pass through the one-quarter wave plate 56, thereby rotating the polarization axis of the beam 28. A preferred rotation amount may be a quarter rotation. After reflecting from a focal point in the patient's eye, a returning reflected portion of the beam 28 may pass back through the one-quarter wave plate 56, thereby further rotating the polarization axis of the returning reflected portion of the beam 28. After passing back through the one-quarter wave plate 56, the returning reflected portion of the beam may experience a total polarization rotation of 90 degrees so that the reflected light from the eye may be fully reflected by the polarized beam-splitter 48. A birefringence of the cornea can also be taken into account if, for example, the imaged structure is the crystalline lens. In this case, the plate 56 can be adjusted and/or configured such that the double pass of the plate 56 as well as the double pass of the cornea sum up to a polarization rotation of 90 degrees. In some embodiments, birefringence of the cornea may be taken into account during imaging of the cornea, as discussed further below with regard to FIG. 7A. Because the birefringence of the cornea may be different from patient to patient, the configuration/adjustment of the plate 56 can be done dynamically so as to optimize the signal returning to the detection sensor 54. In some embodiments, the plate 56 may be rotated at an angle. Accordingly, the returning reflected portion of the beam 28 may be polarized to be at least partially reflected by the polarized beam-splitter 48 so as to be directed through the filter 50, through the lens 51, and to the pinhole aperture 52. The filter 50 can be configured to block wavelengths other than the wavelengths of interest. The pinhole aperture 52 may block any returning reflected portion of the beam 28 reflected from locations other than the focal point from reaching the detection sensor 54. Because the amount of returning reflected portion of the beam 28 that reaches the detection sensor 54 depends upon the nature of the tissue at the focal point of the beam 28, the signal generated by the detection sensor 54 can be processed in combination with data regarding the associated locations of the focal point so as to generate image/location data for structures of the eye.

As shown in the illustrated embodiment, the scanning assembly 18 may include a Z-scan device 58 and an XY-scan device 60. The Z-scan device 58 may be operable to vary a convergence/divergence angle of the beam 28 and thereby change a location of the focal point in the direction of propagation of the beam 28. For example, the Z-scan device 58 may include one or more lenses that are controllably movable in the direction of propagation of the beam 28 to vary a convergence/divergence angle of the beam 28. The XY-scan device 60 may be operable to deflect the beam 28 in two dimensions transverse to the direction of propagation of the beam 28. For example, the XY-scan device 60 can include one or more mirrors that are controllably deflectable to scan the beam 28 in two dimensions transverse to the direction of propagation of the beam 28. Accordingly, the combination of the Z-scan device 58 and the XY-scan device 60 can be operated to controllably scan the focal point in three dimensions, for example, within the eye of the patient.

As shown further in the illustrated embodiment, a camera 62 and associated video illumination 64 can be integrated with the scanning assembly 18. The camera 62 and the beam 28 may share a common optical path through the objective lens assembly 20 to the eye. A video dichroic 66 may be used to combine/separate the beam 28 with/from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

Figure 3:
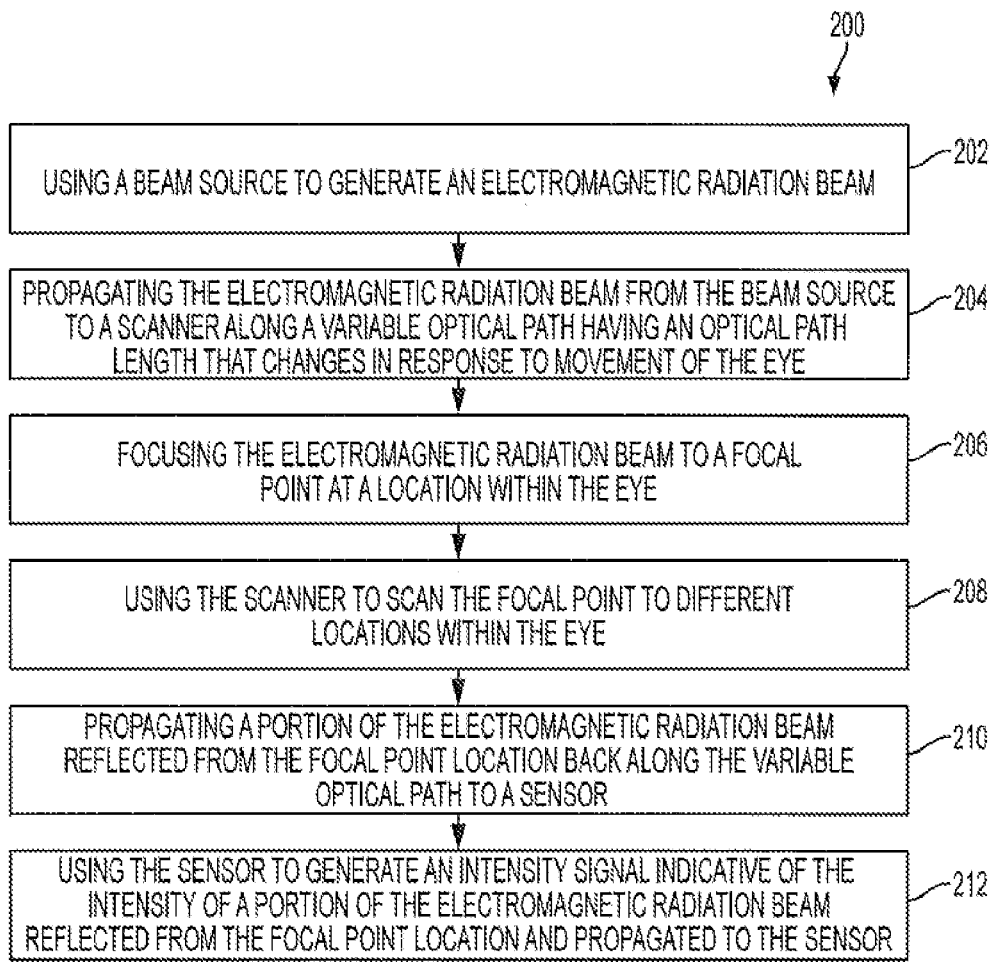
FIG. 3 is a simplified process of imaging and/or modifying an intraocular target according to an embodiment of the invention.

FIG. 3 is a simplified block diagram of acts of a process 200 of the laser surgery system 10 according to many embodiments for imaging an eye. The laser surgery system 10 uses a beam source to generate an electromagnetic radiation beam (Action Block 202). The laser surgery system 10 propagates the electromagnetic radiation beam from the beam source to a scanner along a variable optical path having an optical path length that changes in response to movement of the eye (Action Block 204). The laser surgery system 10 focuses the electromagnetic radiation beam to a focal point at a location within the eye (Action Block 206). A scanner of the laser surgery system 10 scans the focal point to different locations within the eye (Action Block 208). The laser surgery system 10 propagates a portion of the electromagnetic radiation beam reflected from the focal point location back along the variable optical path to a sensor (Action Block 210). The sensor generates an intensity signal indicative of the intensity of a portion of the electromagnetic radiation beam reflected from the focal point location and propagated to the sensor (Action Block 212).

Figure 4:
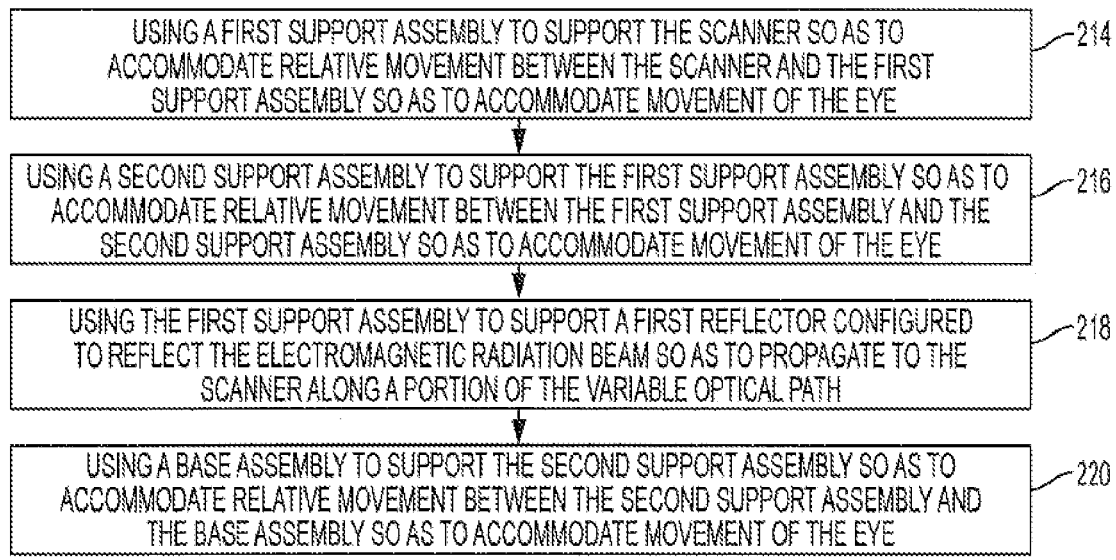

FIGS. 4, 5, and 6 illustrates options that may be accomplished as part of the process 200. For example, the laser surgery system 10 may include a first support assembly for supporting the scanner to accommodate movement of the eye (Action Block 214). The laser surgery system 10 may also use a second support assembly to further support the first support assembly to accommodate movement of the eye (Action Block 216). The first support assembly supports a first reflector configured to reflect the electromagnetic radiation beam so as to propagate to the scanner along a portion of the variable optical path (Action Block 218). A base assembly supports the second support assembly to accommodate movement of the eye (Action Block 220). The second support assembly may support a second reflector configured to reflect the electromagnetic radiation beam to propagate along a portion of the variable optical path so as to be incident on the first reflector (Action Block 222). The sensor generates the intensity signal by passing a reflected portion of the electromagnetic radiation beam through an aperture to block portions of the electromagnetic radiation beam reflected from locations other than the focal point location (Action Block 224). The electromagnetic radiation beam passes through a polarization-sensitive device (Action Block 226) which modifies the polarization of at least one of the electromagnetic radiation beam and a portion of the electromagnetic radiation beam reflected from the focal point location (Action Block 228). The polarization-sensitive device reflects a portion of the electromagnetic radiation beam reflected from the focal point location so as to be incident upon the sensor (Action Block 230).

Figure 7A:
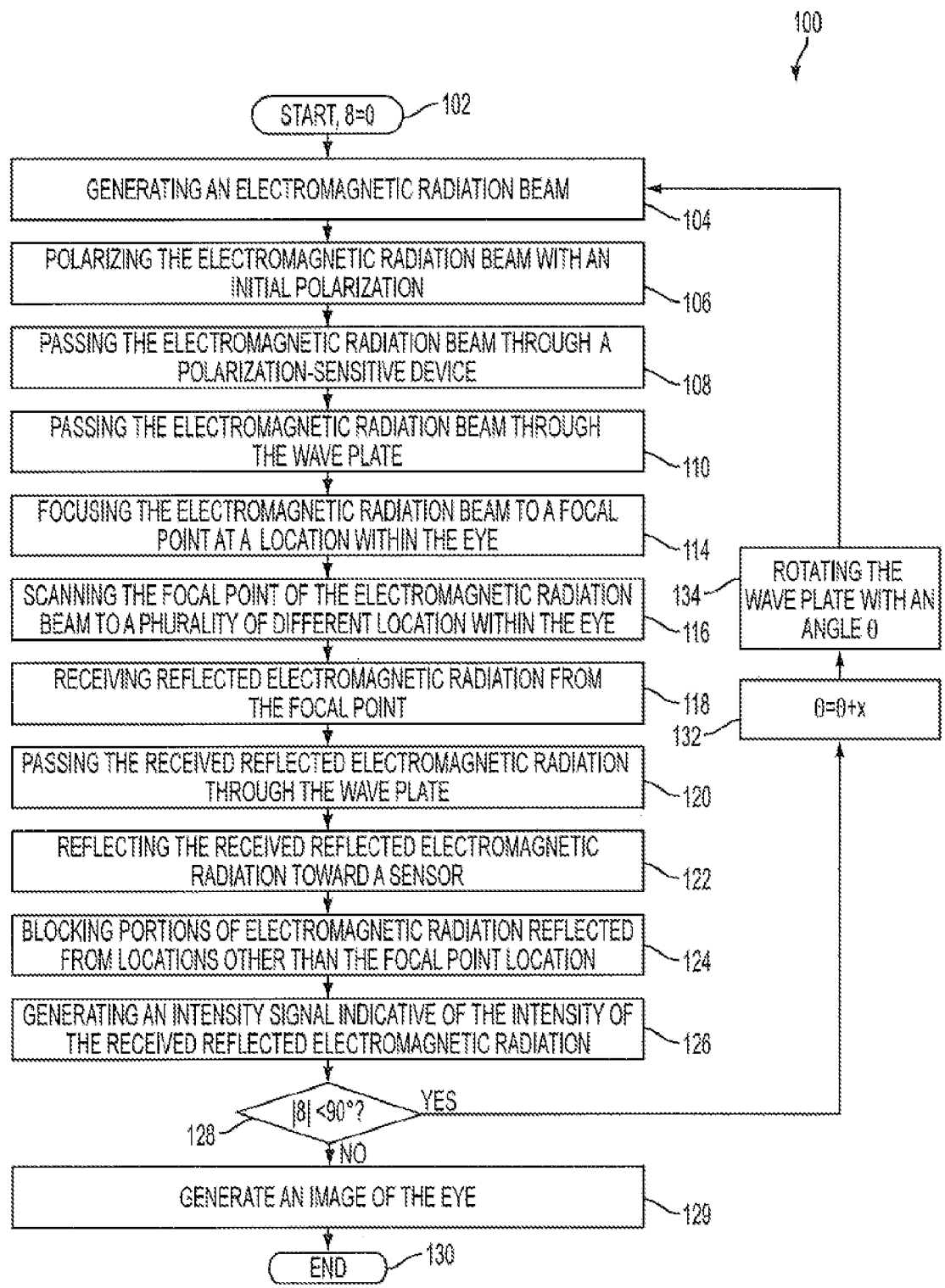
FIG. 7A is a process for imaging an eye, according to an embodiment of the invention.

FIG. 7A shows a process 100 of a laser surgery system for imaging a cornea of an eye according to some embodiments of the invention. In some situations, it may be desirable to accurately image the cornea with a confocal detector. Further, it may be desirable to accurately identify or detect the anterior and posterior boundaries of the cornea, for example, to determine a thickness of the cornea. The intensity of a confocal signal may change substantially between the front of the cornea and the back of the cornea, which can make detection more difficult than would be ideal. This change in intensity may be related to local changes in birefringence of the cornea, which may cause signal loss at a confocal detector. Additionally, in at least some eyes, the birefringence properties of the cornea may vary with corneal depth. Further, corneal birefringence properties may vary laterally and radially in unpredictable amounts. Thus, in some embodiments, the light passing back through the one-quarter wave plate may be rotated by an angle other than ninety degrees on the second pass through a polarizing beam-splitter, such that some of the light is reflected toward the light source instead of toward the sensor. The process 100 provided in FIG. 7A may address some of the difficulties of imaging the back surface of the cornea. Process 100 may start (Action Block 102) with a variable θ equal to zero. The variable θ may represent a rotation angle of the wave plate relative to an initial position of the wave plate. Accordingly, the wave plate may be at an initial position at the start (Action Block 102) of process 100. The laser surgery system generates an electromagnetic radiation beam using a beam source, e.g., laser 32 (Action Block 104). The electromagnetic beam is polarized (Action Block 106) with an initial polarization. The electromagnetic radiation beam passes through a polarization-sensitive device (Action Block 108) and through the wave plate (Action Block 110). The electromagnetic radiation beam may be focused to a focal point at a location within the eye (Action Block 114), and may scan the focal point to a plurality of different locations within the eye (Action Block 116). In response to focusing the electromagnetic radiation beam and/or scanning the focal point of the electromagnetic radiation, electromagnetic radiation may be reflected from the focal point and received by the laser surgery system (Action Block 118). The received reflected electromagnetic radiation may be passed through the wave plate (Action Block 120), and further reflected by the polarization-sensitive device toward a sensor (Action Block 122). Portions of electromagnetic radiation reflected from locations other than the focal point location may be blocked (Action Block 124), for example, by an aperture. An intensity signal indicative of the intensity of the received reflected electromagnetic radiation may be generated by the sensor (Action Block 126). Once the magnitude of angle θ is greater than or equal to ninety degrees (e.g., the wave plate has rotated ninety degrees from the initial position of the wave plate) (Decision Block 128), the laser surgery system generates an image of the eye (Action Block 129 and End 130). If the magnitude of angle θ is less than ninety degrees (Decision Block 128), variable θ may be increased by an incremental amount x. The wave plate may be mechanically rotated by a rotation angle θ (Action Block 134). Thereafter, the laser surgery system may loop back and repeat Action Blocks 104-126 with the wave plate rotated by an angle θ. Process 100 may end when steps 104-126 are performed with the wave plate rotated by ninety degrees from the initial position of the wave plate.

As should be appreciated, in an embodiment of process 100, the laser surgery system 10 scans the eye with focal points of more than one electromagnetic radiation beam, where the electromagnetic radiation beams have varying degrees of polarization due to a varying wave plate orientation. The plurality of scans, and hence the plurality of intensity signals, may help compensate for difficulties in imaging the anterior and posterior surface of the cornea due to the birefringence of the cornea. Some intensity signals may include strong intensity signals from an anterior portion of a cornea of the eye. Other intensity signals may include strong intensity signals from posterior portions of the cornea. In some embodiments, the plurality of intensity signals may be used in-part or in whole to form a composite signal to accurately identify anterior and posterior details of a cornea, such as the anterior and posterior surfaces. Accordingly, the plurality of scans may compensate for imaging signal loss due to local cornea birefringence properties.

In many embodiments, the above methods may be performed by the laser surgery system 10 illustrated in FIG. 1 and FIG. 2. For example, laser 32 may be used to perform step 104. Polarizer and beam dump device 42 may be used to perform step 106. At step 108, the electromagnetic radiation beam may pass through the polarized beam-splitter 48. The one-quarter wave plate 56 may be used to modify the initial polarization of the electromagnetic radiation beam to perform step 110. XY-scan device 60 and Z-scan device 58 may be used to perform step 114 and step 116. At step 120, the one-quarter wave plate 56 may be used to receive and modify a polarization of the reflected electromagnetic radiation. The polarized beam-splitter 48 may be used to reflect the reflected electromagnetic radiation toward a sensor at step 122. Pinhole aperture 52 may be used to perform step 124 and detector 54 may be used to perform step 126. In some embodiments, laser surgery system 10 may be preprogrammed to perform multiple scans according to method 100.

Figure 7B:
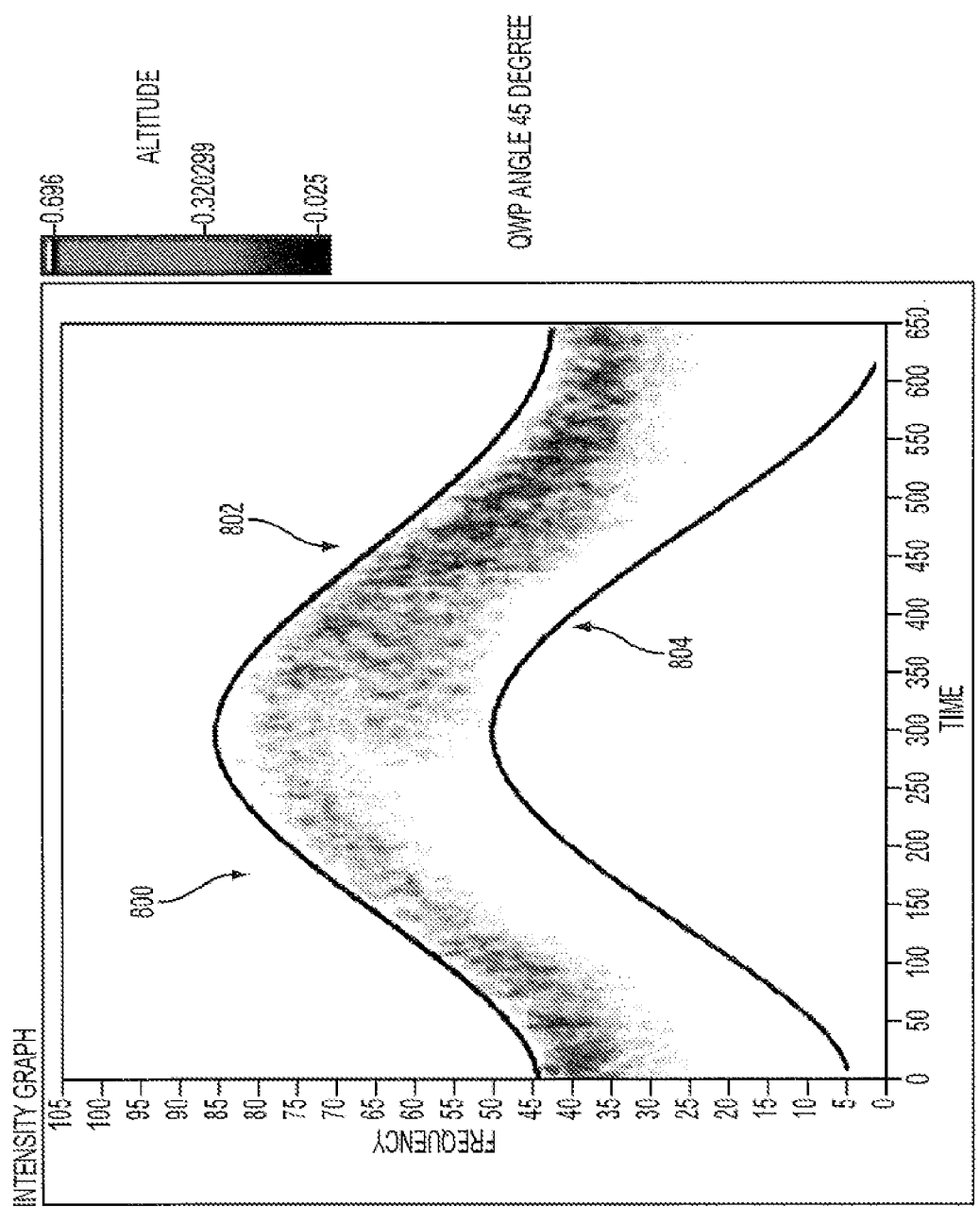
FIGS. 7B-7C show two exemplary intensity profiles of a cornea of an eye generated according to the process shown in FIG. 7A.
Figure 7C:
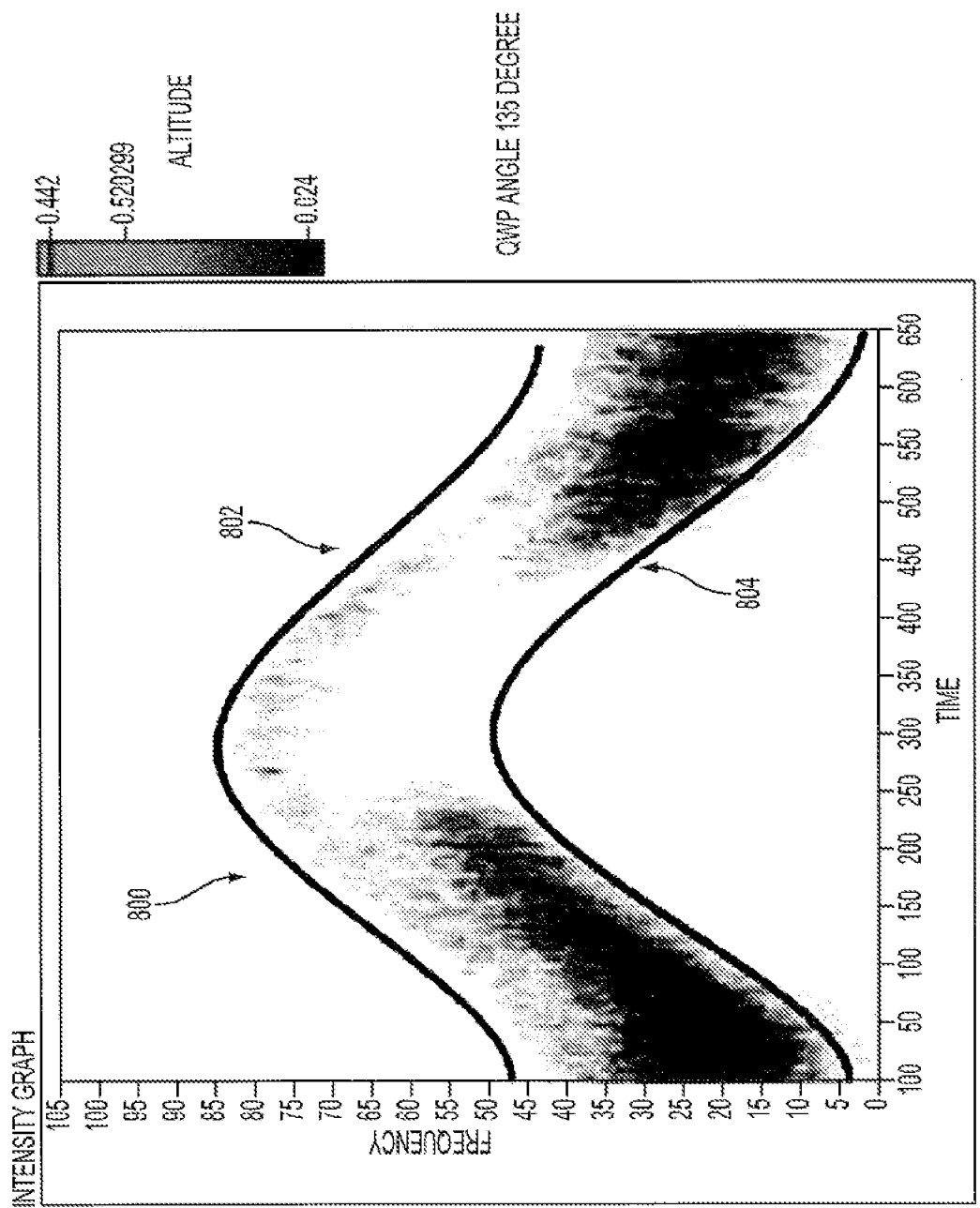

Variable x may be any incremental value. In some embodiments, x may be one, two, three, five, fifteen, thirty, forty-five, or ninety degrees. In some situations, it may be desirable to perform process 100 quickly. Optionally, process 100 may be completed with two scans when x is ninety degrees. In such an embodiment, the eye may be scanned twice with an electromagnetic radiation beam focal point. This may be done preferably to minimize the effects of inadvertent eye movement relative to the imaging system between or during sequential scans. FIG. 7B and FIG. 7C illustrate two exemplary intensity profiles from a cornea 800 generated by such a process. FIG. 7B shows a generated intensity profile of reflected electromagnetic radiation from a cornea 800 when the one-quarter wave plate has an initial position of forty-five degrees. As can be seen, the scan in FIG. 7B may include an intensity profile with higher intensity at an anterior surface 802 of the cornea 800, but may have lower intensity toward some portions of the posterior surface 804 of the cornea 800. The intensity signal toward the posterior surface 804 of the cornea 800 may decrease toward the peripheral edge of the cornea 800. After the scan illustrated in FIG. 7B, a second scan illustrated in FIG. 7C may be performed. FIG. 7C shows a generated intensity profile of reflected electromagnetic radiation from the cornea 800 after the one-quarter wave plate is rotated ninety degrees from the initial position to one hundred thirty-five degrees. As can be seen, the scan in FIG. 7C may include an intensity profile with lower intensity at an anterior surface 802 of the cornea when the one-quarter wave plate is rotated to one hundred thirty five degrees. The scan in FIG. 7C, however, may include an intensity profile with higher intensity at portions of the posterior surface 804 of the cornea 800. In particular, the scan in FIG. 7C may provide an intensity profile with higher intensity at the posterior surface of the cornea 800 and near the peripheral edge of the cornea 800. Accordingly, the two scans shown in FIGS. 7B and 7C may be used together to account for local variations and to more accurately identify both the anterior surface 802 and the posterior surface 804 of the cornea 800. Optionally, a corneal thickness may be accurately calculated thereafter.

The surface profile of a cornea can be measured in one or more of many ways, and may comprise one or more of an anterior corneal surface topography profile, a posterior a corneal surface topography profile, or a corneal thickness profile as obtained from the generated intensity profiles. In many embodiments, the surface profile comprises a representation of a three dimensional profile and may comprise an extraction of one or more parameters from one or more images, such as an extraction of keratometry values from a corneal topography system or tomography system integrated with the surgical laser. The one or more parameters can be used to determine a tissue treatment pattern on the eye, such as the angular location, depth, arc length and anterior to posterior dimensions of incisions. For instance, the surface profile can be used to determine an axis of treatment of a plurality of arcuate incisions, the plurality of arcuate incisions extending along an arc transverse to the axis of treatment.

In many embodiments, the optical surface of the eye is fit with one or more with one or more of a Fourier transform, polynomials, a spherical harmonics, Taylor polynomials, a wavelet transform, or Zernike polynomials. The optical tissue surface may comprise one or more of the anterior surface of the cornea, the posterior surface of the cornea, the anterior surface of the lens capsule, the posterior surface of the lens capsule, an anterior surface of the lens cortex, a posterior surface of the lens cortex, an anterior surface of the lens nucleus, a posterior surface of the lens nucleus, one or more anterior surfaces of the lens having a substantially constant index of refraction, one or more posterior surfaces of the lens having a substantially constant index of refraction, the retinal surface, the foveal surface, a target tissue surface to correct vision such as a target corneal surface, an anterior surface of an intraocular lens, or a posterior surface of an intraocular lens, for example.

Figure 8:
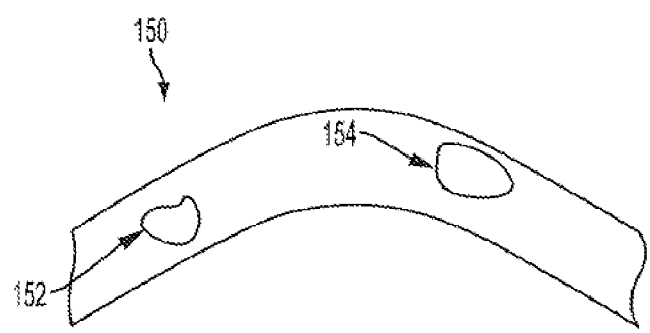
FIG. 8 is an exemplary illustration showing a plurality of regions of the cornea of an eye, wherein according to an embodiment of the invention, the regions may have varying birefringence properties.

In an embodiment, a cornea 150, as illustrated in FIG. 8, may have a first region 152 with a first birefringence and a second region 154 with a second birefringence. Thus, in imaging the cornea, a first electromagnetic radiation beam may be directed through the first region 152 of the cornea 150 to a first location in the eye. The first electromagnetic radiation beam may have a first polarization. A second electromagnetic radiation beam may be directed through the second region 154 of the cornea 150 to a second location in the eye. The second electromagnetic radiation beam may have a second polarization different than the first polarization. An image of the eye encompassing the first and second locations may be generated using electromagnetic radiation signals reflected from the eye in response to the steps of directing the first and second electromagnetic radiation beams. As such, the laser surgery system 10 may provide a single composite image that uses a plurality of beams with varying polarization to account for local differences in corneal birefringence properties.

Figure 9:
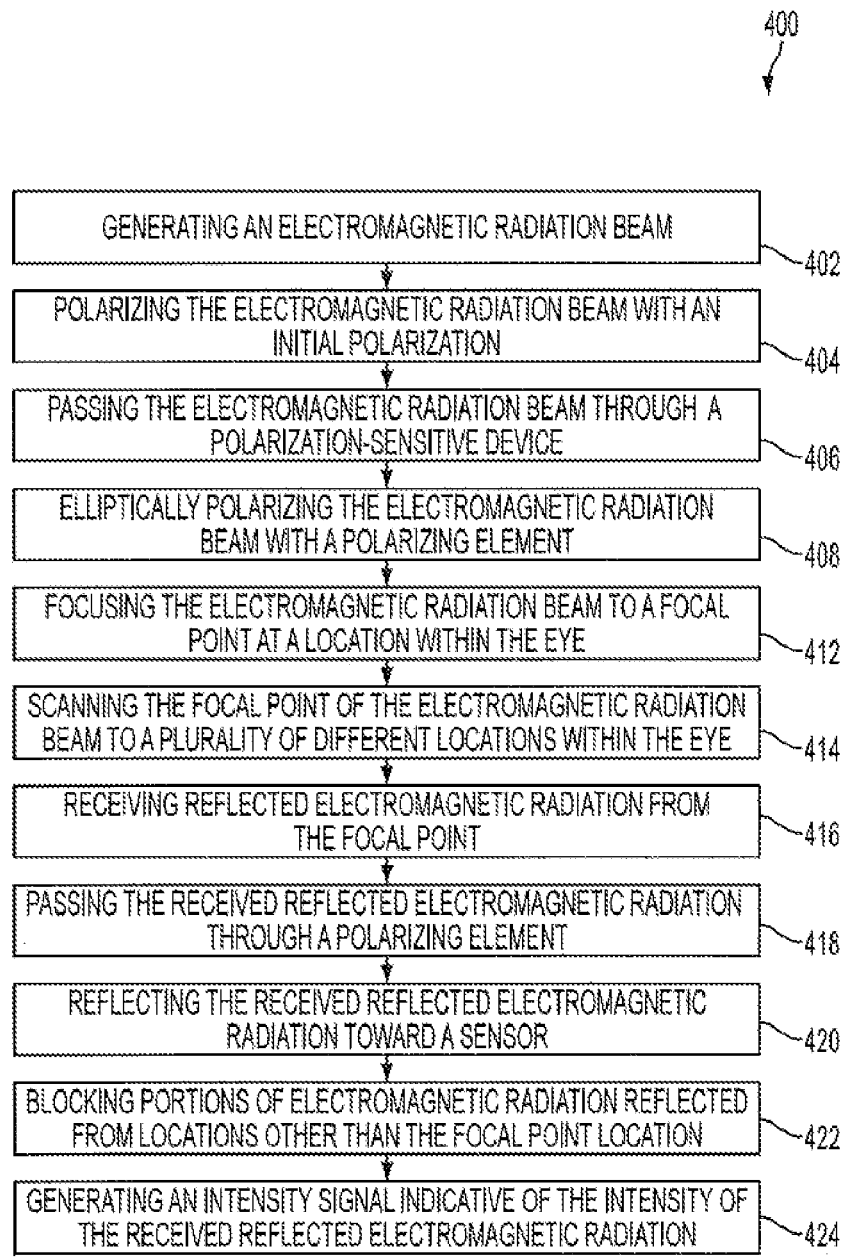
FIG. 9 is another process for imaging an eye according to an embodiment of the invention.

FIG. 9 shows another process 400 of the laser surgery system 10 for imaging a cornea of an eye according to some embodiments of the invention. In some situations, process 400 may be used to compensate for birefringence of the cornea to accurately identify its anterior and posterior boundaries. The laser surgery system 10 generates an electromagnetic radiation beam (Action Block 402), which may be polarized with an initial polarization (Action Block 404). The electromagnetic radiation beam passes through a polarization-sensitive device (Action Block 406) and is elliptically polarized (Action Block 408). The laser system surgery 10 focuses the elliptically polarized electromagnetic radiation beam to a focal point at a location within the eye (Action Block 412), and scans the focal point to a plurality of different locations within the eye (Action Block 414). The laser system surgery 10 receives reflected electromagnetic radiation from the focal point (Action Block 416). The received reflected electromagnetic radiation passes through the polarizer (Action Block 418) and is reflected or directed toward a sensor (Action Block 420). The laser surgery system 10 may block portions of electromagnetic radiation reflected from locations other than the focal point location (Action Block 422). The laser surgery system 10 may generate an intensity signal that is indicative of the intensity of the received reflected electromagnetic radiation.

In an embodiment of the process 400, the laser surgery system 10 may use elliptically polarized light to identify and/or image the anterior and posterior portions of a cornea because, for example, elliptically polarized light will not produce linearly polarized light at one angle on the second pass through the beam-splitter such that the signal will change with less depth.

Figure 10A:
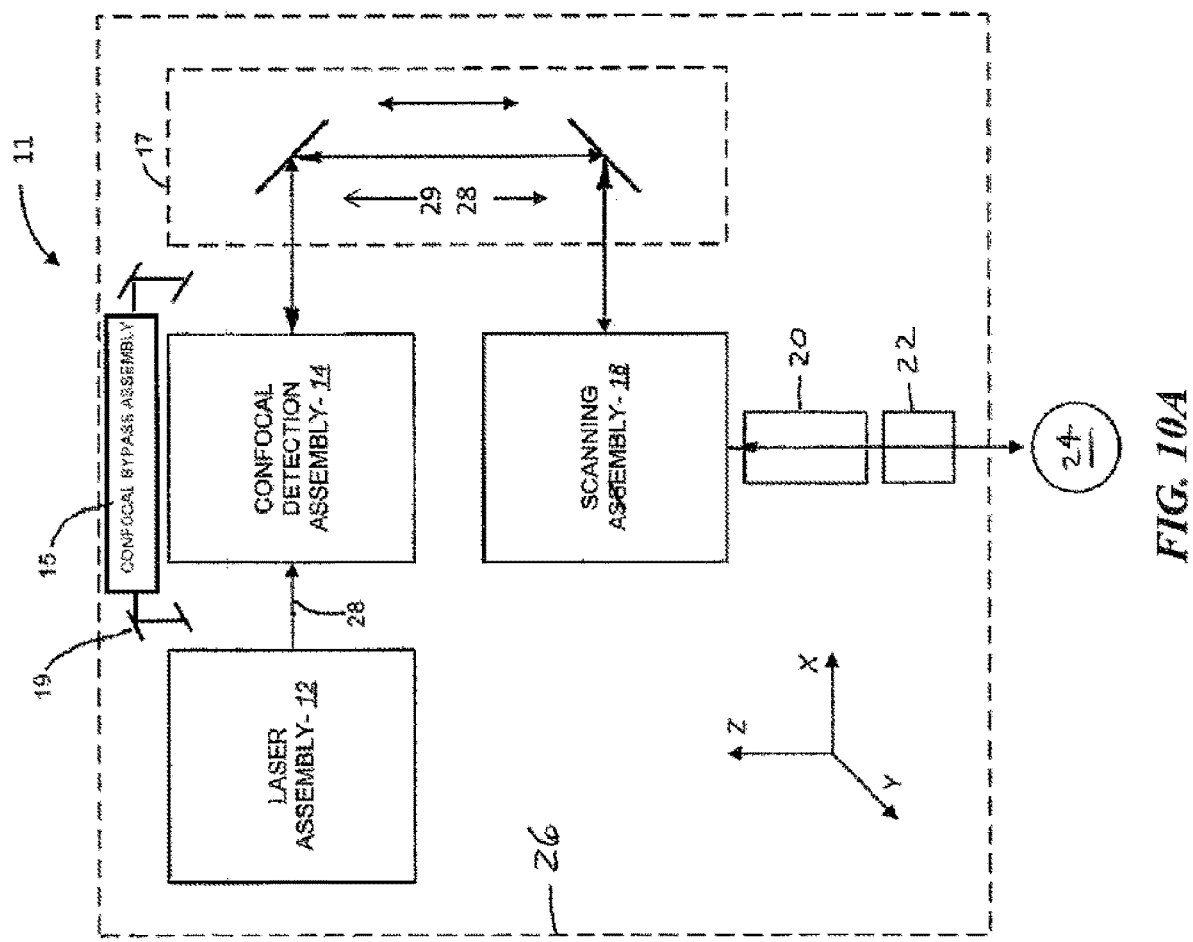
FIG. 10A and FIG. 10B are a schematic diagrams of a laser surgery system according to another embodiment.
Figure 10B:
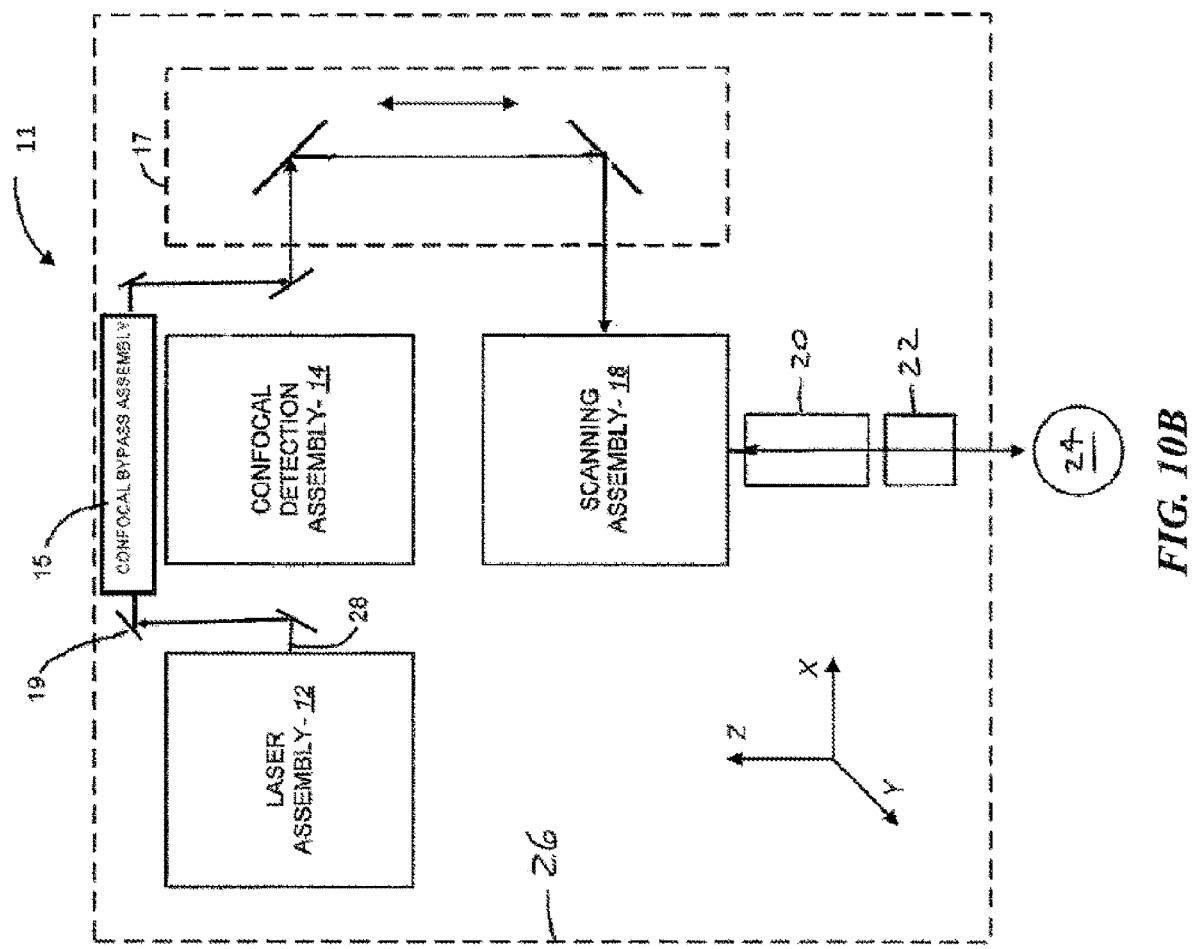

FIG. 10A and FIG. 10B schematically illustrate a laser surgery system 11 according to many embodiments. The laser surgery system 10 includes a laser assembly 12, a confocal detection assembly 14, confocal bypass assembly 15, a transfer optical path 17, a scanning assembly 18, an objective lens assembly 20, and a patient interface device 22. The laser surgery system 11 includes elements as described in the laser surgery system 10, as shown in FIG. 2. The confocal bypass assembly 15 generally includes at least one optical element 19 and is operable to reversibly divert the optical path of reflected electromagnetic beam 29 (a portion of electromagnetic beam 28) around at least one optical element (not shown) that delivers a portion of a reflected electromagnetic beam 29 to a sensor in the confocal detection assembly 14. By bypassing the optical element of the confocal detection assembly 14, the imaging system is inactivated because the reflected light 29 is not diverted to a sensor in the confocal bypass assembly 14. In the embodiment shown in FIG. 10A, the confocal bypass assembly 15 is represented in a state where it is not actively operating to divert the optical path of electromagnetic beam 28, and so in FIG. 10A, a portion of reflected electromagnetic beam 29 is shown propagating from transfer optical path 16 to the confocal detection assembly 14, thereby rendering the imaging system of the laser surgery system 10 operable. This may be referred to as an "imaging mode" of laser surgery system 100.

When operating according to the embodiment of FIG. 10A, the electromagnetic beam is preferably configured so as to not modify tissue. For example, the electromagnetic beam can be attenuated or otherwise modified to have an energy level below a threshold level for tissue modification. Alternatively, the electromagnetic beam can be configured to modify tissue even in the imaging mode.

In a preferred embodiment of an imaging mode, a portion of the electromagnetic beam 28 is reflected by eye tissue at the focal point and propagates along the optical bath back to the confocal detection assembly 14. Specifically, a reflected portion 29 of the electromagnetic beam 28 travels back through the patient interface device 22, back through the objective lens assembly 20, back through (and de-scanned by) the scanning assembly 15, back through the transfer optical path 15, and to the confocal detection assembly 14. In many embodiments, and as will be discussed further herein, the reflected portion 29 of the electromagnetic beam 28 that travels back to the confocal detection assembly confocal detection assembly is directed to be incident upon a sensor that generates an intensity signal indicative of intensity of the incident portion of the electromagnetic beam. The intensity signal, coupled with associated scanning of the focal point within the eye, can be processed in conjunction with the parameters of the scanning to, for example, image/locate structures of the eye, such as the anterior surface of the cornea, the posterior surface of the cornea, the iris, the anterior surface of the lens capsule, and the posterior surface of the lens capsule.

Transfer optical path 17 generally comprises one or more optical elements that guide beam 28 from the confocal detection assembly 14 or the confocal bypass assembly 15 to the scanning assembly 18. It should be noted that while transfer optical path 17 is shown as a separate component of the laser surgical system 10 of FIG. 1A, the transfer optical path 17 is optional. In other embodiments transfer optical path 17 may serve a variety of other function. For example, in another embodiment, transfer optical path 17 may comprise or be substituted by a free-floating mechanism 16 described in connection with the embodiment of FIG. 2.

FIG. 10B schematically illustrates the laser surgery system 11 of FIG. 1A when the confocal bypass assembly 15 is placed in the optical path of electromagnetic beam 28. In FIG. 10B, the confocal bypass assembly 15 is operable to reversibly divert the optical path of electromagnetic beam 28 along an alternative optical path (i.e., a diversion optical path) that diverts the beam 28 around at least an optical element (not shown) of the confocal detection assembly 14 such that a reflected portion of electromagnetic beam 28 is not diverted to a sensor in the confocal detection assembly 30. In the embodiment of FIG. 10B, the confocal bypass assembly 15 is represented in a state where it is actively operating to divert the optical path of electromagnetic beam 28, and so in FIG. 10B, the electromagnetic beam 28 is shown propagating from laser assembly 20 along an optical path through the confocal bypass assembly 15 and around the optical element (not shown) of the confocal bypass assembly 14 such that no portion of electromagnetic beam 28 is directed to a sensor (detector) of the confocal detection assembly 14. This may be referred to herein as a "non-imaging mode" or alternatively, as a "treatment mode" of laser surgery system 10.

In many embodiments of the treatment mode of FIG. 10B, the beam 28 emitted by the laser assembly 20 propagates along a fixed optical path through the confocal bypass assembly 15 to the transfer optical path 17. Upon reaching the transfer optical path 17, the beam 28 propagates through the remaining laser surgical system in a manner that is the same or similar to the embodiment of FIG. 10A. Specifically, beam 28 travels along transfer optical path 17, is delivered in turn to the scanning assembly 18 and propagates through the objective lens assembly 20, through the interface device 22, and to the patient 24 as described with respect to FIG. 10A.

It should be noted that, in the embodiment of FIG. 10B, a portion of the electromagnetic beam 28 may be reflected by patient tissue at the focal point and propagate along the optical path back along the optical path by which it was delivered. Specifically, a reflected portion of the electromagnetic beam 28 travels back through the patient interface device 22, back through the objective lens assembly 20, back through (and de-scanned by) the scanning assembly 18, and back through the transfer optical path 17. However, the reflected beam enters the confocal bypass assembly 15, which again diverts the optical path of electromagnetic beam 28 around the at least one optical element of the confocal detection assembly 14 along the diversion optical path such that the reflected light is not detected by the confocal detection assembly 14.

When operating in the treatment mode, the direction and position of beam 28 is preferably the same or substantially the same at the entry of and at the exit from the diversion optical path, in a plane transverse to the direction of propagation of the electromagnetic beam. The direction and position of beam 28 is deemed substantially the same at the entry of and at the exit from the diversion optical path in a plane transverse to the direction of propagation of the electromagnetic beam so long as the beam properties are sufficient to meet the system level targeting specification.

Further, the direction and position of beam 28 at the exit from the diversion optical path of confocal bypass assembly 14 in the treatment mode is the same or substantially the same as the direction and position of beam 28 at the same position in the optical path in imaging mode in a plane transverse to the direction of propagation of the electromagnetic beams 28.

When operating in a treatment mode, the electromagnetic beam 28 is preferably configured so as to be capable of modifying tissue. For example, the electromagnetic beam preferably has an energy level above a threshold level for tissue modification.

Figure 11:
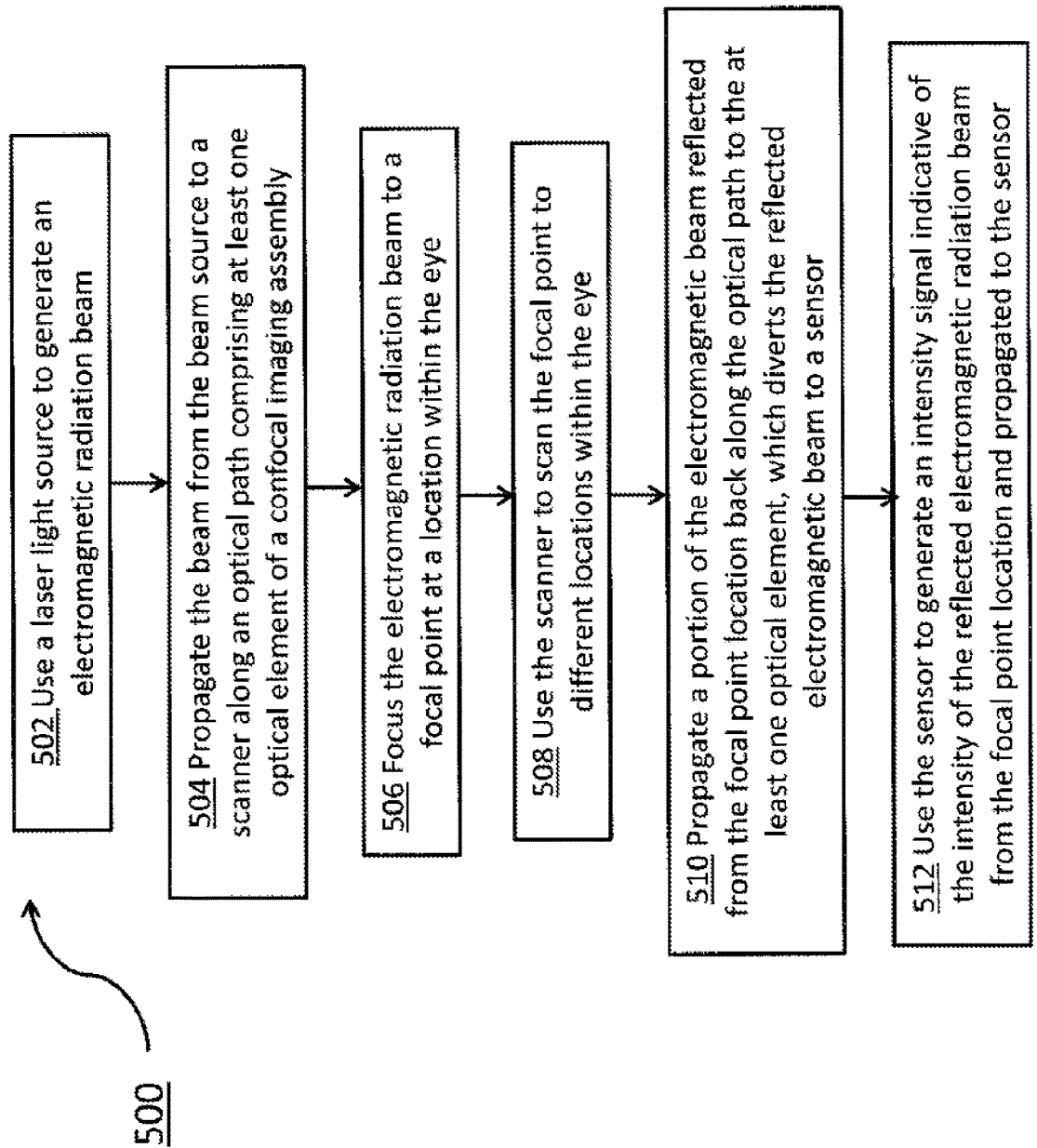
FIG. 11 is a simplified block diagram of acts of a method according to many embodiments, in which the laser surgery system is used to image one or more portions of a target tissue, such as a patient's eye.

FIG. 11 is a simplified block diagram of acts of a process 500 according to a method of imaging an eye in accordance with an imaging mode. Any suitable device, assembly, and/or system, such as described herein, can be used to practice the process 500. The process 500 includes using a beam source to generate an electromagnetic beam (Action Block 502) and propagating the electromagnetic beam from the beam source to a scanner along an optical path comprising at least one optical element of a confocal imaging assembly (Action Block 504). The process 500 includes focusing the electromagnetic beam to a focal point at a location within the eye (Action Block 506). The process 500 includes using the scanner to scan the focal point to different locations within the eye (Action Block 508). The process 500 includes propagating a portion of the electromagnetic beam reflected from the focal point location back along the optical path to the at least one optical element, which diverts the reflected electromagnetic radiation to a sensor (Action Block 510). The process 500 includes using the sensor to generate an intensity signal indicative of the intensity of the reflected electromagnetic beam from the focal point location and propagated to the sensor (step 512).

Figure 12:
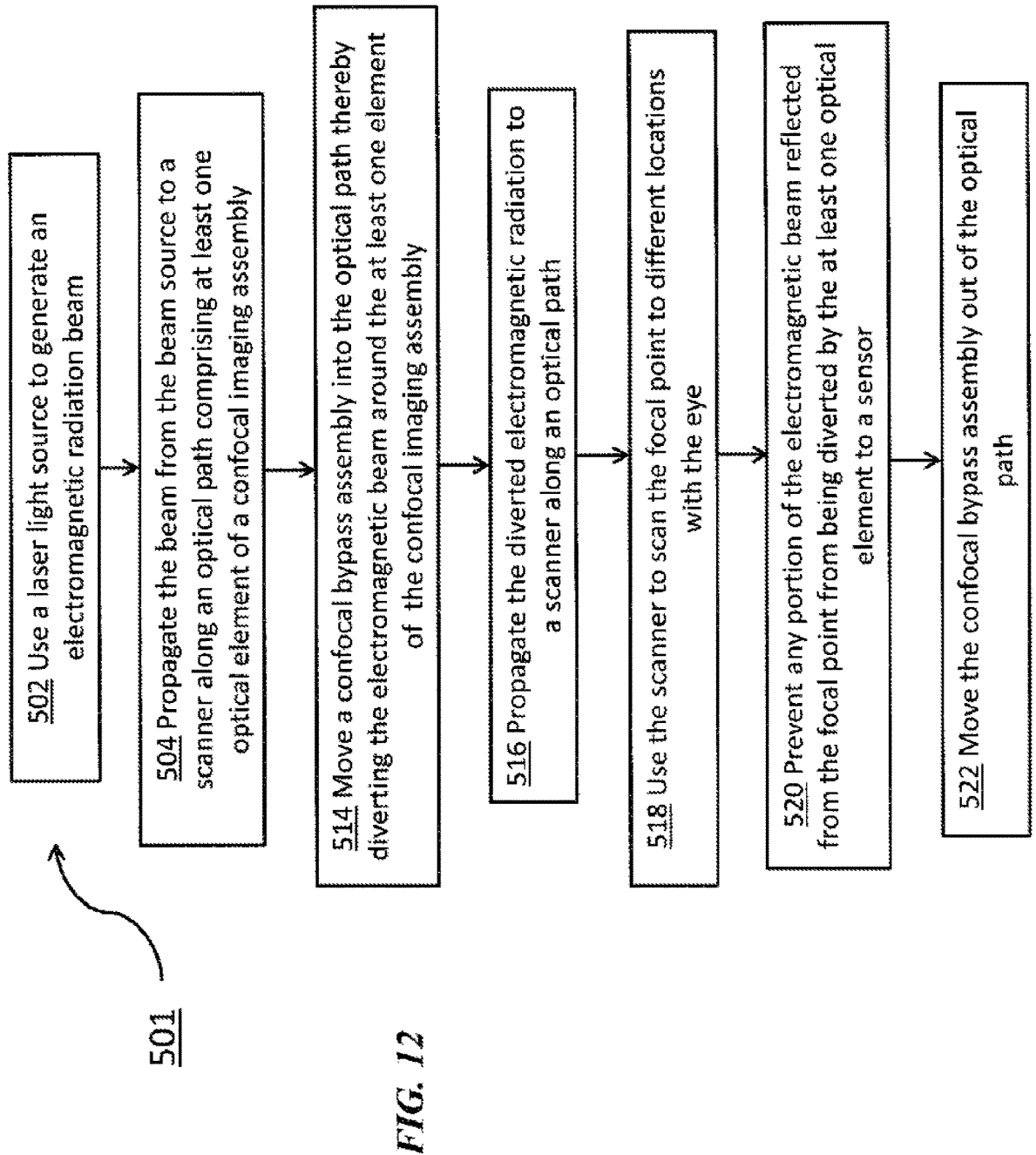
FIG. 12 is as simplified block diagram of acts according to many embodiments, in which the laser surgery system is used to modify target tissue in a patient's eye.

FIG. 12 is a process 501 for reversibly switching operation from an imaging mode to a non-imaging mode may include using a laser source to generate an electromagnetic beam (Action Block 502), propagating the electromagnetic beam from the beam source along an optical path comprising at least one optical element of a confocal imaging assembly (Action Block 504), moving a confocal bypass assembly into the optical path thereby diverting the electromagnetic beam around the at least one element of the confocal imaging assembly (Action Block 514), propagating the diverted electromagnetic radiation to a scanner (Action Block 516), using the scanner to scan the focal point to different locations with the eye (Action Block 518) and, preventing any portion of the electromagnetic beam reflected from the focal point location from being diverted by the at least one optical element to a sensor of the confocal bypass assembly (Action Block 520) and moving the confocal bypass assembly out of the optical path (Action Block 522).

Figure 13:
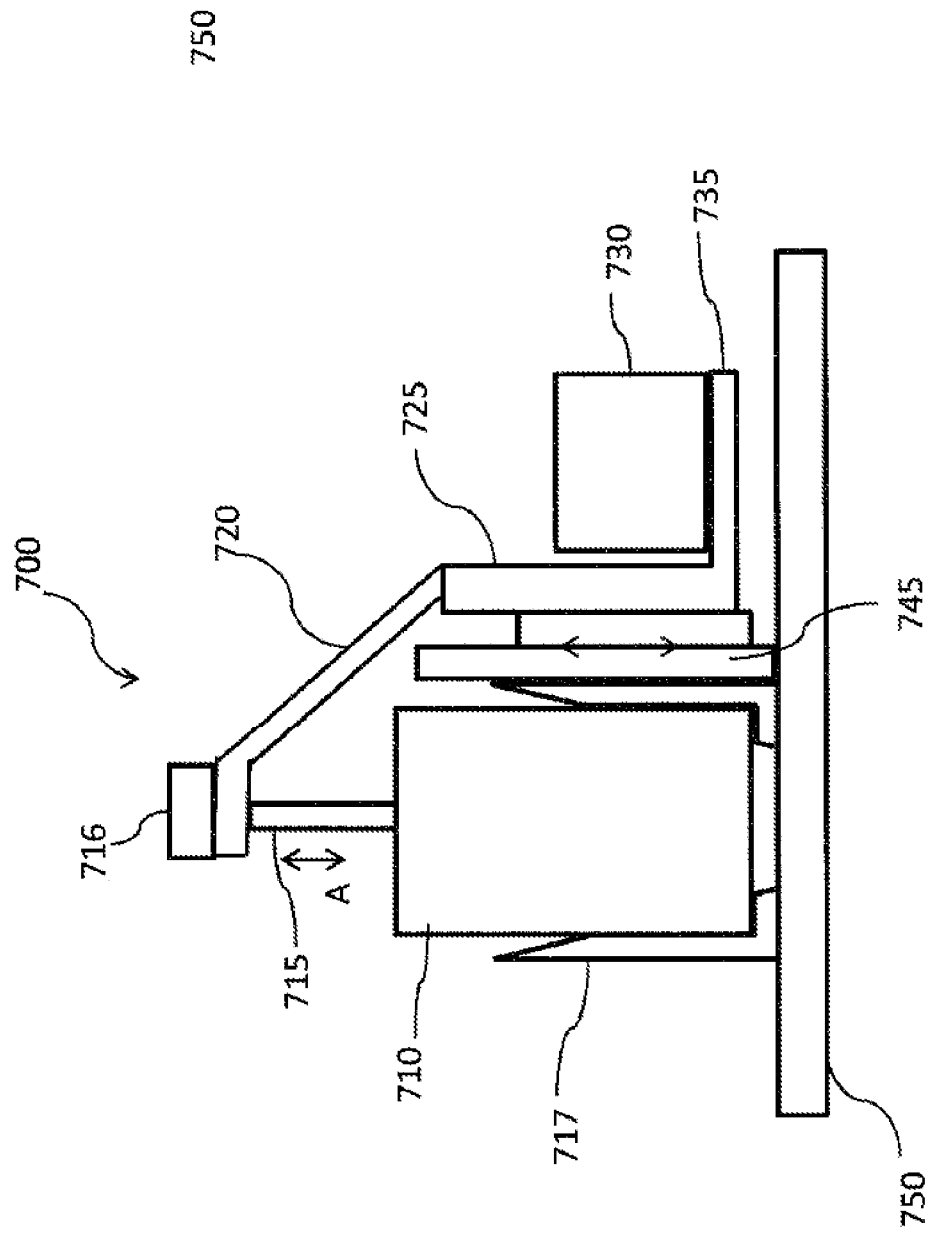
FIG. 13 is a schematic diagram showing an illustrative embodiment of a confocal bypass assembly.

One embodiment of a confocal bypass assembly 700 is shown in FIG. 13. The confocal bypass assembly 700 includes a push solenoid 710 having an arm 715 that is fixably connected to one end of actuation arm 720 and is secured in place by a tip 716. In the embodiment of FIG. 5, push solenoid 710 is held in a frame 417, which is fixably mounted to base 750. Arm 715 of the push solenoid reversibly moves in the "A" direction. The other end of actuation arm 720 is connected to a carrier 725, which has a platform 735 on which the bypass optical element 730 is mounted. The confocal bypass assembly 700 may also include a slide member 745 having 2 sides that move relative to teach other along the "A" direction. In the embodiment of FIG. 5, the carrier 725 is fixably connected to one side of slide 745, and frame 717 holding push solenoid 710 is fixably connected the other side of slide 745 such that the push solenoid and the carrier move in the direction "A" relative to each other.

In operation, in the embodiment of FIG. 5, arm 715 of push solenoid 410 moves in the direction "A" away from the body of the push solenoid, and the movement of the arm 715 is communicated to the carrier 725 via actuation arm 720 and results in the movement of carrier 725 in the same "A" direction relative to the body of the push solenoid by action of the slide 745. In this way, the bypass optical element 730 is raised into the optical path of the electromagnetic path of the electromagnetic beam. The bypass optical element 730 may then be removed from the optical path by moving the arm 715 of the push solenoid 710, under control of control electronics towards the body of the push solenoid 710, thus reversing the movement of bypass optical element 735 and thus moving it out of the optical path of the beam 28.

The confocal bypass assembly generally includes one or more optical elements, referred to herein as bypass optical element optical elements, which, when inserted into the optical path of the electromagnetic beam, divert the beam around at least one optical element of the confocal detection assembly. The confocal bypass assembly thus establishes an alternative optical path, referred to herein as a diversion optical path, around the one or more optical elements of the confocal detection assembly. The confocal bypass assembly should thus be configured to reversibly move one or more bypass optical elements into and out of the optical path of the electromagnetic beam under control of system control electronics when an imaging mode or treatment mode is desired. Those of ordinary skill in the art will recognize that the reversible movement of an optical elements into and out of an optical path thus may be accomplished in numerous ways.

In a preferred embodiment, the bypass optical element is a bypass prism designed to divert beam 28 around an optical element of the confocal detection assembly by a series of reflections within the bypass prism. In one embodiment, the bypass prism is comprised of two rhomboid prisms, which may optionally be joined together to form a single integrated unit. Alternatively, a set of mirrors can be used to divert the beam around the optical element of the confocal detection assembly.

Figure 14B:
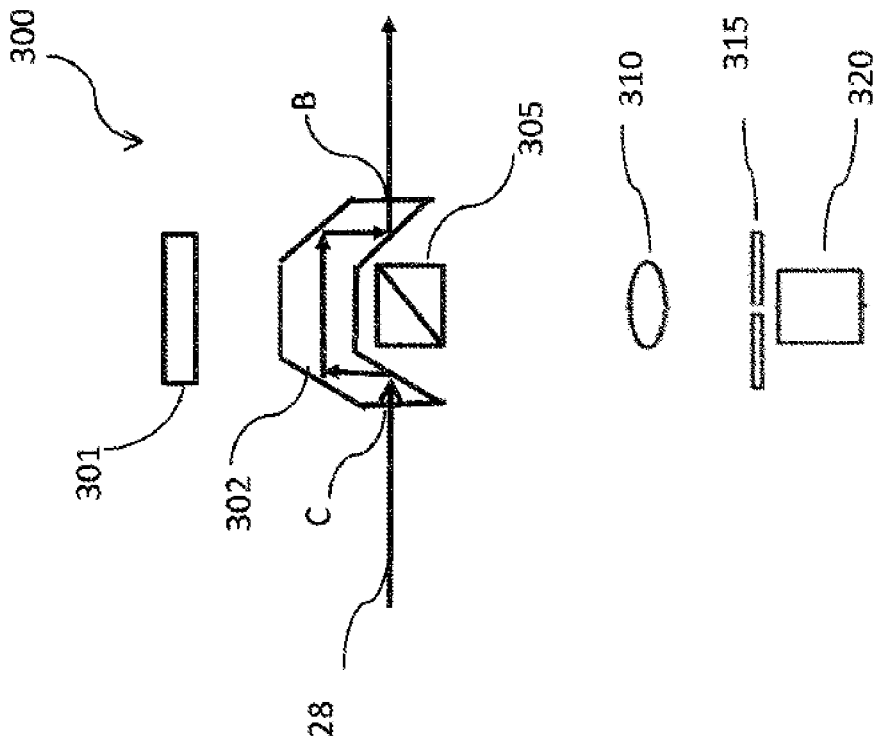
FIG. 14A and FIG. 14B are schematic diagrams illustrating an embodiment, in which the confocal bypass assembly includes a bypass prism, and wherein the optical path in an imaging mode is illustrated in FIG. 14A, and a diversion optical path in a non-imaging mode (i.e. treatment mode) is illustrated in FIG. 14B.
Figure 14A:
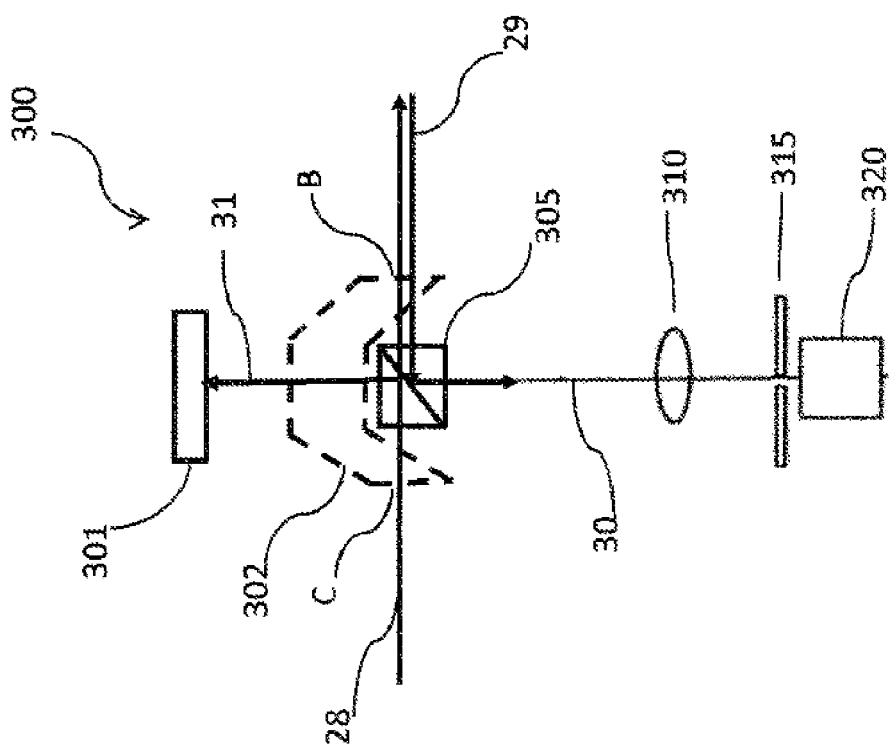

FIGS. 14A and 14B show certain aspects of a laser surgical system showing the operation of a confocal bypass assembly comprising a bypass prism as the bypass optical element. In FIG. 14A, the bypass element is below the optical beam 28 and is shown in dashed lines to demonstrate its relative position to the confocal detection assembly when viewed from above. Since the confocal bypass assembly is not in the optical path in FIG. 14A, FIG. 14A shows a mode of the system wherein imaging is enabled. In FIG. 14A, electromagnetic beam 28 passes through a beam-splitter (BS) 305 and is then delivered to the scanner and objective which focuses the light on the target tissue (not shown). Returned scattered light 29 from the target tissue is again directed through a beam-splitter 305 and is directed to a focusing lens 310, a pinhole aperture 315 and a sensor (photodetector) 320.

Preferably, the beam-splitter 305 is configured to attenuate the beam 28 such that the beam-splitter 305 transmits only a fraction of the electromagnetic beam 28 to the target resulting in a high power rejected beam 31 directed to dump 301 as the remainder of electromagnetic beam 28 propagates from the light source to the scanner. Preferably, the beam-splitter transmits less than 20% of the incident light, more preferably less than 90%, more preferably less than 95% and more preferably 99% or less of the incident light. Further, the beam-splitter 310 is configured to have a high reflectivity of the returned scattered light 29 directed to the sensor 320. Preferably, the beam-splitter reflects 80% of the reflected light, more preferably 90% of the reflected light, more preferably 95% of the reflected light, and more preferably, 99% or more of the reflected light. Thus, in the imaging mode of FIG. 14A, beam 28 exiting the beam-splitter 305 is attenuated and optimized for imaging. Beam 28 exiting the beam-splitter 305 need not be sufficient to modify the target tissue, and in a preferred embodiment beam 28 is not configured to modify the target tissue as it exits beam-splitter 305 and propagates toward the target tissue.

Preferably, beam-splitter 305 is fixed in the optical path of beam 28 and is not a polarizing beam-splitter (i.e., it does not operate to split a beam based on a polarization property of the reflected light). More preferably, beam-splitter 305 is beam-splitter prism.

FIG. 14B shows a bypass prism 302 inserted into the optical path adjacent the beam-splitter 305. When the bypass prism 302 is inserted in the optical path of beam 28, as shown in FIG. 14B, the beam 28 enters the diversion optical path at point C and is directed around the beam-splitter by bypass prism 302 by undergoing a series of reflections within the body of bypass prism 302 that form the diversion optical path before exiting the bypass prism at point B. The precise number of reflections needed to establish the optical path is not necessarily limited; however, the total number of reflections should be an even number so that the position, direction and orientation of the beam 28 remain the same at the point it enters the bypass optical path (point C in FIG. 14B) and the point it exits the optical path (Point B in FIG. 14B). In FIG. 14B, a series of 4 reflections are shown and each reflection angle is represented as being at right angles, but, while preferred, neither of these is required. Those of ordinary skill will recognize that the diversion optical path may be constructed with various optical elements to achieve an even number of reflections along the diversion optical path using various reflection angles.

Preferably, the direction and orientation of electromagnetic beam 28 remain the same or substantially the same at the point it exits the bypass optical path (point B in FIG. 14B), and the same position in the optical path of the imaging mode (Point B in FIG. 14A). "Substantially the same" means that the beam properties are sufficient to meet the system level targeting specification.

By diverting beam 28 around beam-splitter 305, the power attenuation of the beam-splitter prism 300 is avoided and the required boresight accuracy relative to the imaging light path, and the laser beam is directed toward the microscope objective to focus on the target. Preferably, in the treatment mode of FIG. 14B, the electromagnetic beam is configured to modify the target tissue.

Figure 15A:
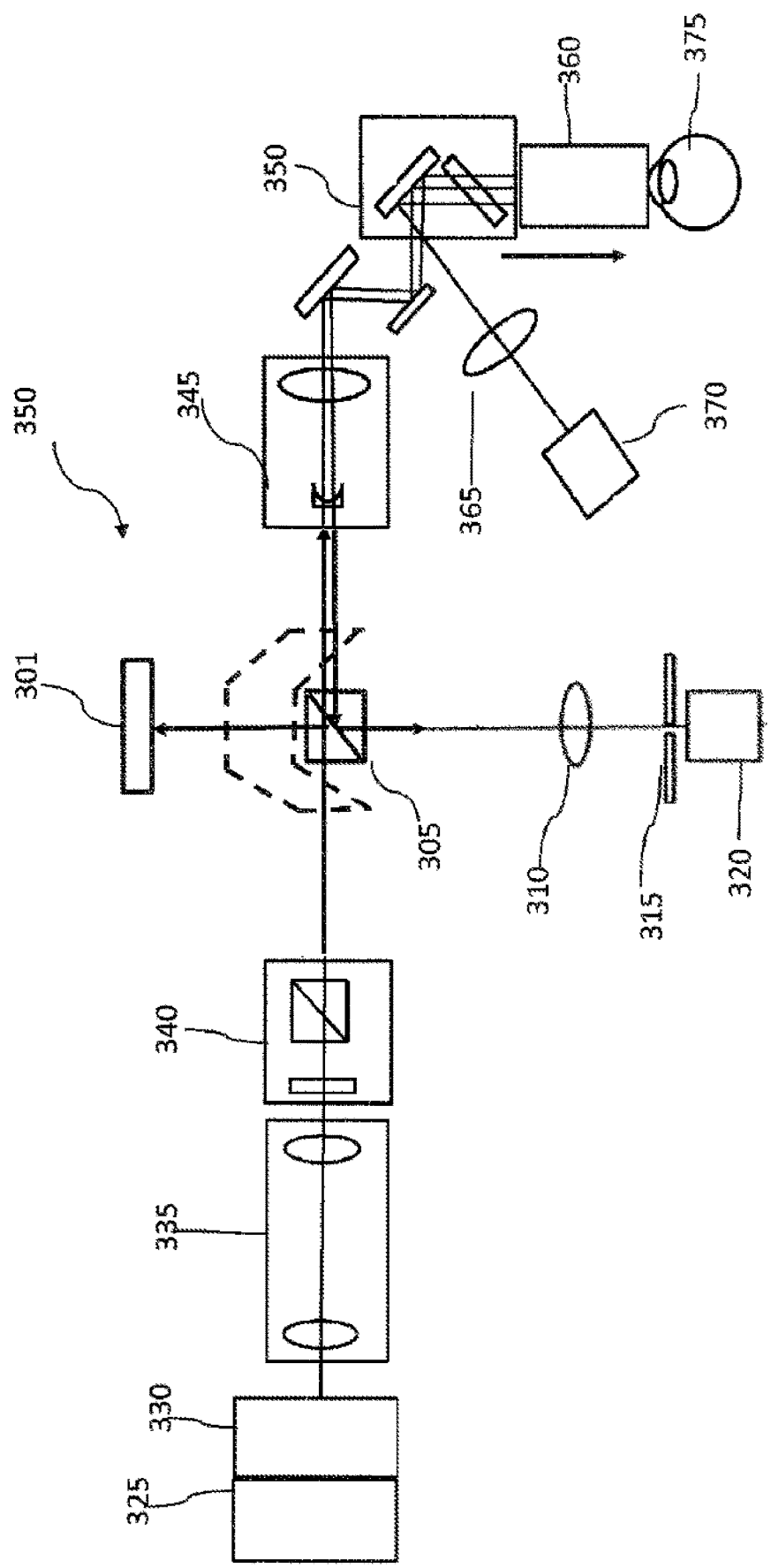
FIG. 15A and FIG. 15B are schematic diagrams illustrating an embodiment of a laser surgical system utilizing a bypass prism to switch between an imaging mode (FIG. 15A) and a non-imaging mode (FIG. 15B).
Figure 15B:
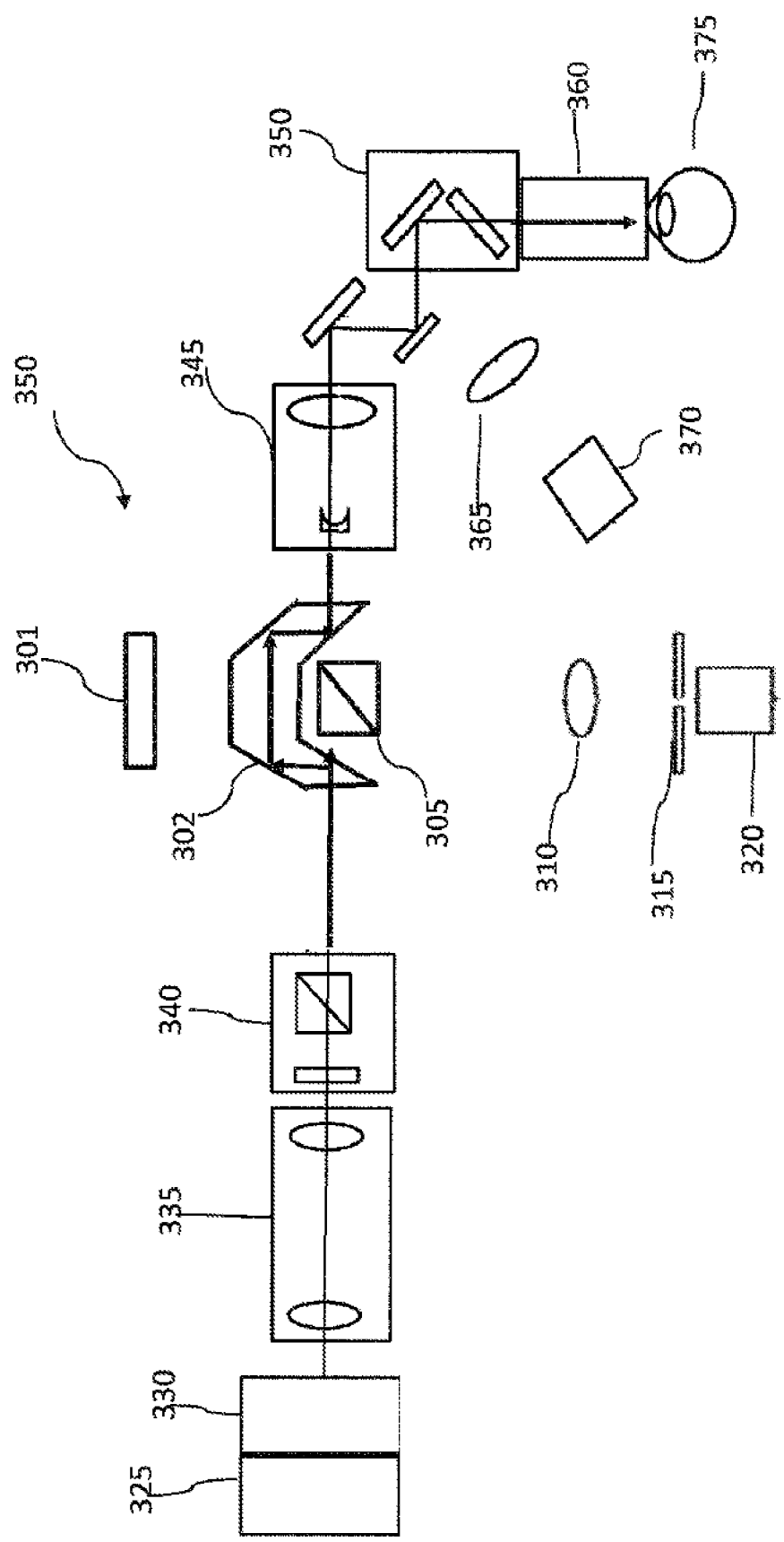

One implementation of a system using a bypass prism and a confocal bypass assembly is shown in FIG. 15A and FIG. 15B. The system 350 includes control electronics 325, a light source 320, an optional attenuator 340, a beam expander 335, an optional optical variable beam attenuator 340, a separate focus lens combination 345 and a scanning means 350. The light beam 328 of light source 320 is propagated though beam-splitter and is focused through lens 360 to its target location 375. Additionally, the reflected light from the target structure 375 is again directed through the beam-splitter 305 and diverted to lens 310. An aperture pinhole 315 is placed in the focal spot of reflected beam as a conjugate of the laser beam focus in target structure 375. The intensity of the reflected electromagnetic beam through beam aperture 315 is detected and converted to an electrical signal which can be read by the control unit 325. In the embodiment of FIG. 15A and FIG. 15B, an image of the treated area is imaged by lens 365 on an image capture device 370 which can be a CCD or a CMOS camera. Also this signal is transmitted to control unit 325.

Figure 16:
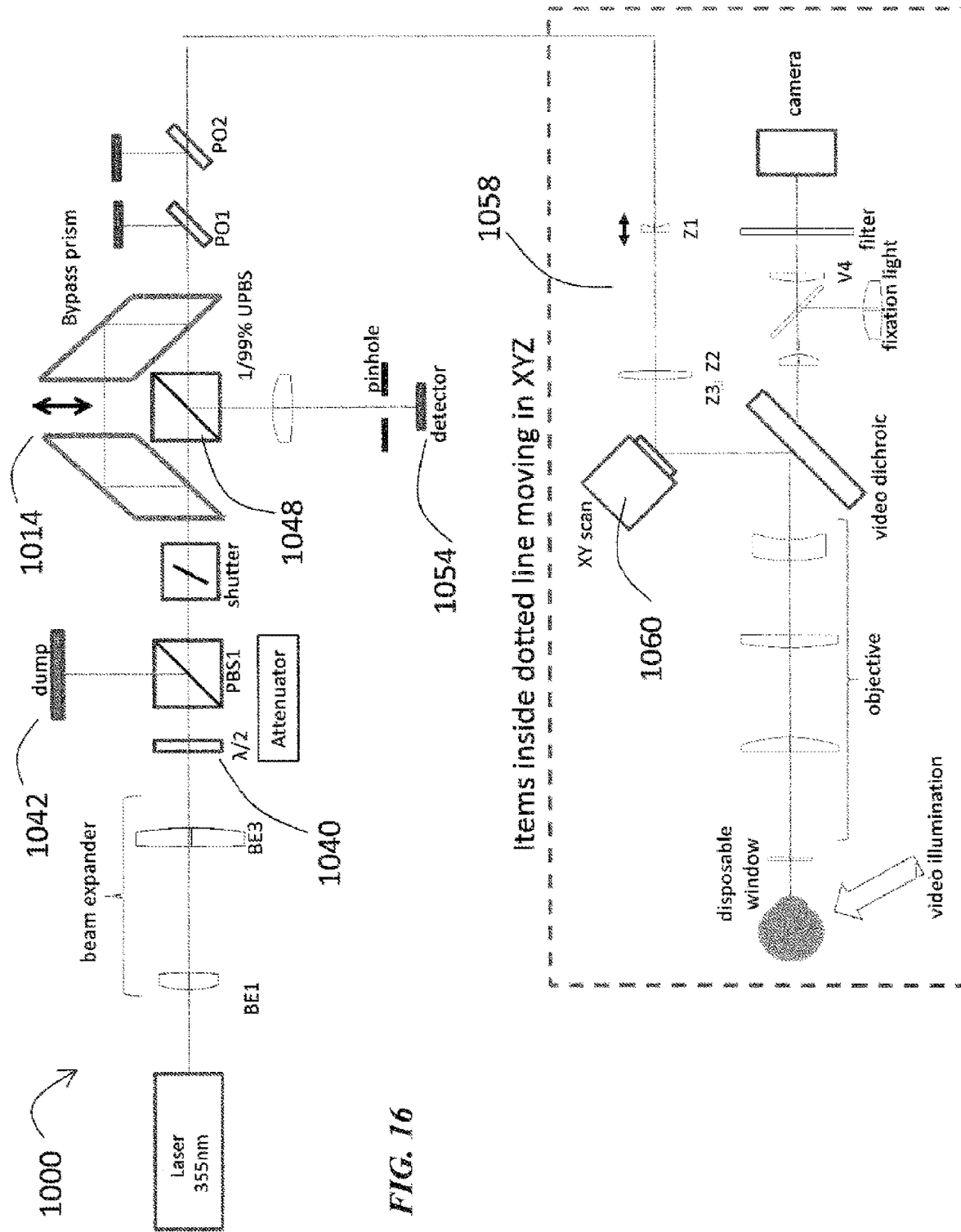
FIG. 16 is another schematic diagram of the laser surgery system of FIG. 1, according to an embodiment of the invention.

FIG. 16 illustrates a laser surgery system 1000 used for imaging and treating an eye according to another embodiment that includes a bypass assembly. The laser surgery system 1000 includes elements as described in the laser surgery system 10, as shown in FIG. 2. The laser surgery system 1000 further may manage the different power levels required for imaging at low levels and treating at high levels and at the same time switching between imaging and treatment optical path. At the same time, this should be done in a manner which makes the whole assembly insensitive to mechanical design choices. The laser surgery system 1000 may further include imaging ocular structures in a low power imaging mode to determine the location of reference surfaces and then using this information to treat in a second high power treatment mode.

In an embodiment, the laser surgery system 1000 does not make use of a polarizing element to avoid issues which arise with the polarization rotation of the cornea. This is achieved by utilizing a high ratio non-polarizing beam-splitter 1048 to separate said beams for imaging. A high splitting ratio of said beam-splitter 1048 acts in two ways: first, reduction of incident power to a regimen where it can be utilized for safe imaging; and second, acting as a high reflector for the light from imaged structure. A second moveable optical element 1014 is inserted in the beam path to bypass the first high contrast beam-splitter 1048 and redirect all available laser light around said splitter 1048 to enable treatment at high energy levels. This bypass element 1014 may have single or multiple prisms or mirrors. The advantage of using this embodiment lays in its high tolerance to mechanical variations to the moving of the bypass element 1014. One could also just move the high contrast beam-splitter 1048, but the mechanical tolerances to enable this would be quite high. All tolerances are relaxed by an order of magnitude by utilizing the bypass assembly 1014.

In an embodiment, the laser surgery system 1000 focuses a first electromagnetic radiation beam to a focal point at a location in the eye, wherein the first electromagnetic radiation beam has a first polarization. The laser surgery system 1000 may further focus a second electromagnetic radiation beam to a focal point at the location in the eye, wherein the second electromagnetic radiation beam has a second polarization state which is different from the first polarization state. The laser surgery system 1000 may further generate a first intensity signal indicative of an intensity of electromagnetic radiation reflected from the eye in response to the step of focusing the first electromagnetic radiation beam, and generate a second intensity signal indicative of an intensity of electromagnetic radiation reflected from the eye in response to the step of focusing the second electromagnetic radiation beam. One or more images of the eye may then be generated with the first and second intensity signals.

In an embodiment, the first and second electromagnetic radiation beams may be focused using a beam scanner. The laser surgery system 1000 may further scan the focal point of the first electromagnetic radiation beam to a plurality of different locations in a first region of the eye and may scan the focal point of the second electromagnetic radiation beam to the plurality of different locations in a second region of the eye. A first intensity profile may be generated that is indicative of intensities of electromagnetic radiation reflected from the eye in response to the step of scanning the focal point of the first electromagnetic radiation beam. A second intensity profile may be generated that is indicative of intensities of electromagnetic radiation reflected from the eye in response to the step of scanning the focal point of the second electromagnetic radiation beam. In an embodiment, one image of the eye is generated using the first and second intensity profiles. For example, in imaging a cornea of an eye, the anterior surface of the cornea may be identified using the first intensity profile and the posterior surface of the cornea may be identified using at least a portion of the second intensity profile. In another embodiment, the first electromagnetic radiation beam has a first polarization; the second electromagnetic radiation beam has a second polarization different than the first polarization.

A beam scanner may include an XY-scan device 1060 that is configured to deflect the first and second electromagnetic radiation beams in two dimensions transverse to a propagation of first and second electromagnetic radiation beams. The focal point of the first and second electromagnetic radiation beam may be scanned in the two dimensions using the XY-scan device 1060 according to some embodiments and may thereby provide an image with at least two dimensions.

The beam scanner may further include a Z-scan device 1058 that is configured to vary a convergence depth of the beam within the eye. In some embodiments, the Z-scan device 1058 may vary a convergence angle of the beam. The focal point of the first and second electromagnetic radiation beams may then be scanned in the three dimensions using the XY-scan device 1060 and the Z-scan device 1058. Accordingly, the image of the eye may be three dimensional according to some embodiments.

In an embodiment, the first and second intensity signals may be generated by a sensor 1054. The sensor 1054 may be a confocal sensor and the laser surgery system 1000 may further block reflected electromagnetic radiation from eye locations other than the location of the focal point of the first and second electromagnetic radiation beams from reaching the sensor 1054.

In an embodiment, the first electromagnetic radiation beam may be generated by passing an electromagnetic radiation beam through a wave plate in a first position, e.g., wave plate 56 as shown in FIG. 2, so as to polarize the electromagnetic radiation beam with the first polarization. The wave plate may be rotated by an angle to a second position. The second electromagnetic radiation beam may be generated by passing the electromagnetic radiation beam through the wave plate in the second position. This wave plate may be a one-quarter wave plate. In some embodiments, the wave plate may be rotated by an acute angle for generating the second electromagnetic radiation beam. In some embodiments, the wave plate may be rotated ninety degrees for generating the second electromagnetic radiation beam. In some embodiments, the first and second electromagnetic radiation beams may be polarized with the first and second polarizations by using a Faraday rotator, or a rotating beam-splitter.

In response to the step of focusing the first electromagnetic radiation beam, the electromagnetic radiation reflected from the eye passes through the wave plate in the first position. Further, electromagnetic radiation reflected from the eye in response to the step of focusing the second electromagnetic radiation beam may be passed through the wave plate in the second position.

In another embodiment, the laser surgery system 1000 may scan a focal point of a first electromagnetic radiation beam to a plurality of locations in the eye, with the first electromagnetic radiation beam having a first polarization. The laser surgery system 1000 may further scan a focal point of a second electromagnetic radiation beam to at least a portion of the plurality of locations in the eye, with the second electromagnetic radiation beam having a second polarization different than the first polarization. A first intensity profile indicative of an intensity of electromagnetic radiation reflected from the eye may be generated in response to the step of scanning the first electromagnetic radiation beam. And a second intensity profile indicative of an intensity of electromagnetic radiation reflected from the eye may be generated in response to the step of scanning the second electromagnetic radiation beam. An image of the eye may be produced using the first and second intensity profiles.

Figure 18:
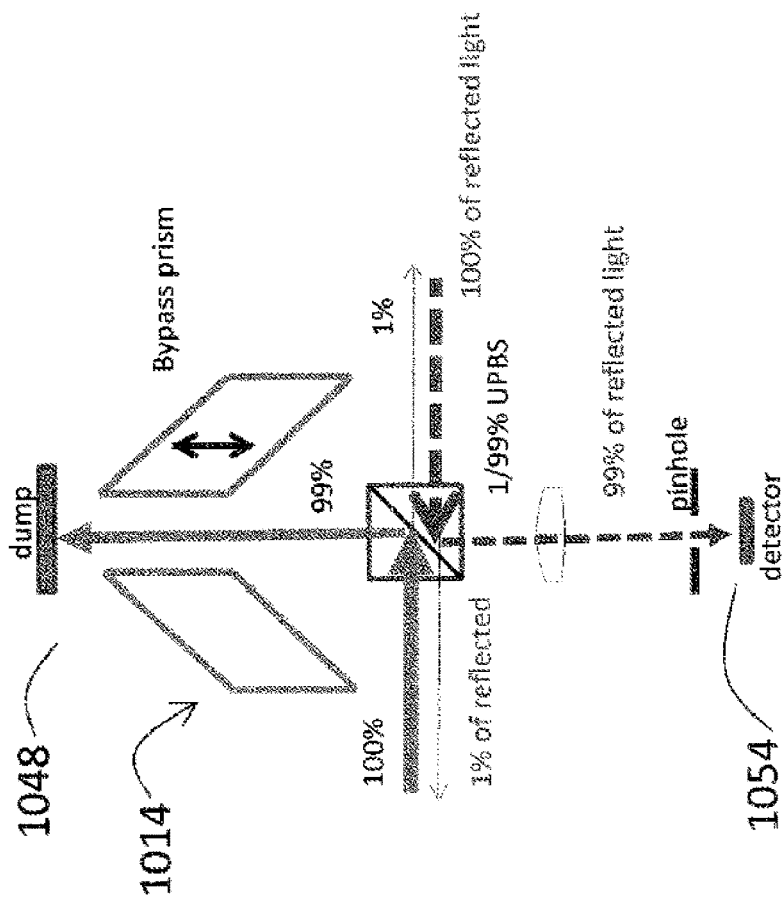
FIG. 18 is another schematic diagram of a bypass element of the laser surgery system of FIG. 10 according to an embodiment of the invention.
Figure 17:
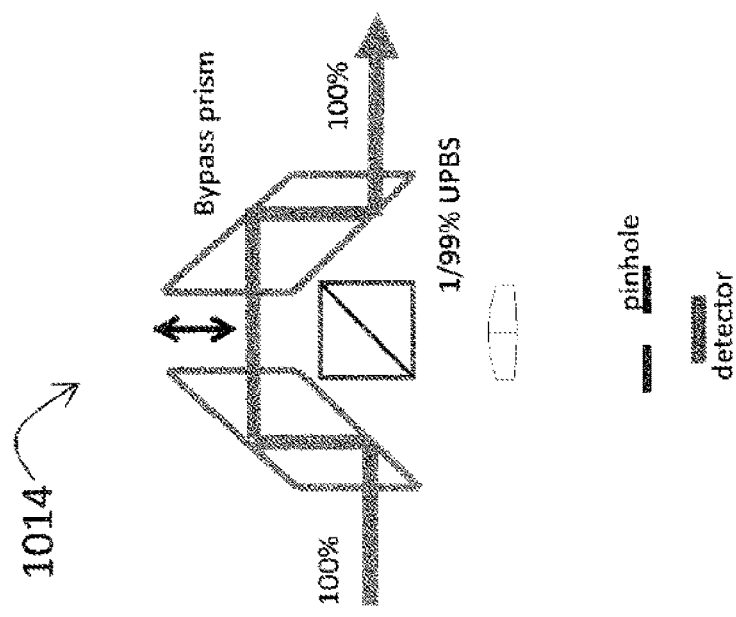
FIG. 17 is a schematic diagram of a bypass element of the laser surgery system of FIG. 10 according to an embodiment of the invention.

FIG. 17 illustrates, according to an embodiment, the bypass assembly 1014 as used in a treatment mode. As shown, the electromagnetic radiation beam is directed toward the bypass mirrors or prisms of the bypass assembly 1014, and bypasses the beam-splitter 1048. As a result, 100% of the electromagnetic radiation beam passes downstream, providing a high power level for treatment mode. FIG. 18 illustrates the system 1000 as used in imaging mode, according to an embodiment. In this embodiment, the electromagnetic radiation beam is directed toward the non-polarized beam-splitter and dump 1048, and bypasses the bypass assembly 1014. The non-polarized beam-splitter is a 1/99% beam-splitter. As a result, 99% of the electromagnetic radiation beam is directed toward the dump, and 1% of the electromagnetic radiation beam passes downstream toward the eye of the patient, resulting in a low power level for imaging. After reflecting from a focal point in the eye of the patient, a returning reflected portion of the beam is again directed by the beam-splitter. As a result, 99% of the reflected portion of the beam is directed upon the sensor 1054 for imaging.

Figure 19:
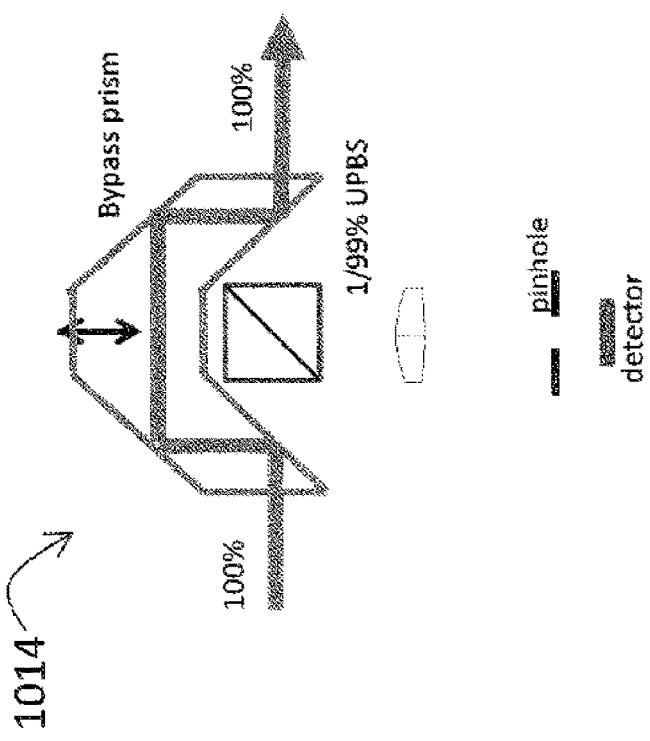
FIG. 19 is another schematic diagram of a bypass element of the laser surgery system of FIG. 10 according to an embodiment of the invention.
Figure 20:
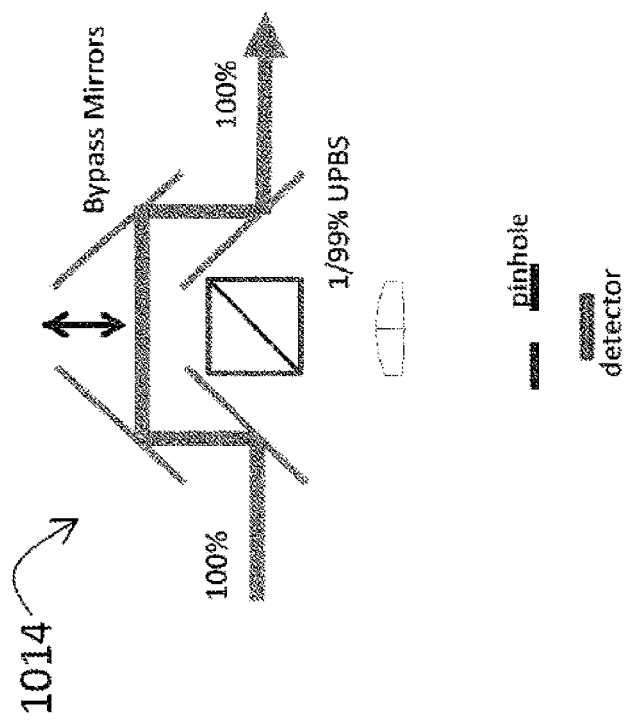
FIG. 20 is another schematic diagram of a bypass element of the laser surgery system of FIG. 10 according to an embodiment of the invention.

It should be noted that other embodiments of the bypass assembly 1014 having single or multiple mirrors or prisms may be used. For example, FIGS. 19 and 20 illustrate other embodiments of the bypass assembly 1014 in treatment mode. In FIG. 19, the two mirrors or prisms positioned at an angle are further connected with a third prism. In FIG. 20, the bypass assembly 1014 utilizes four mirrors or prisms as shown.

Figure 21:
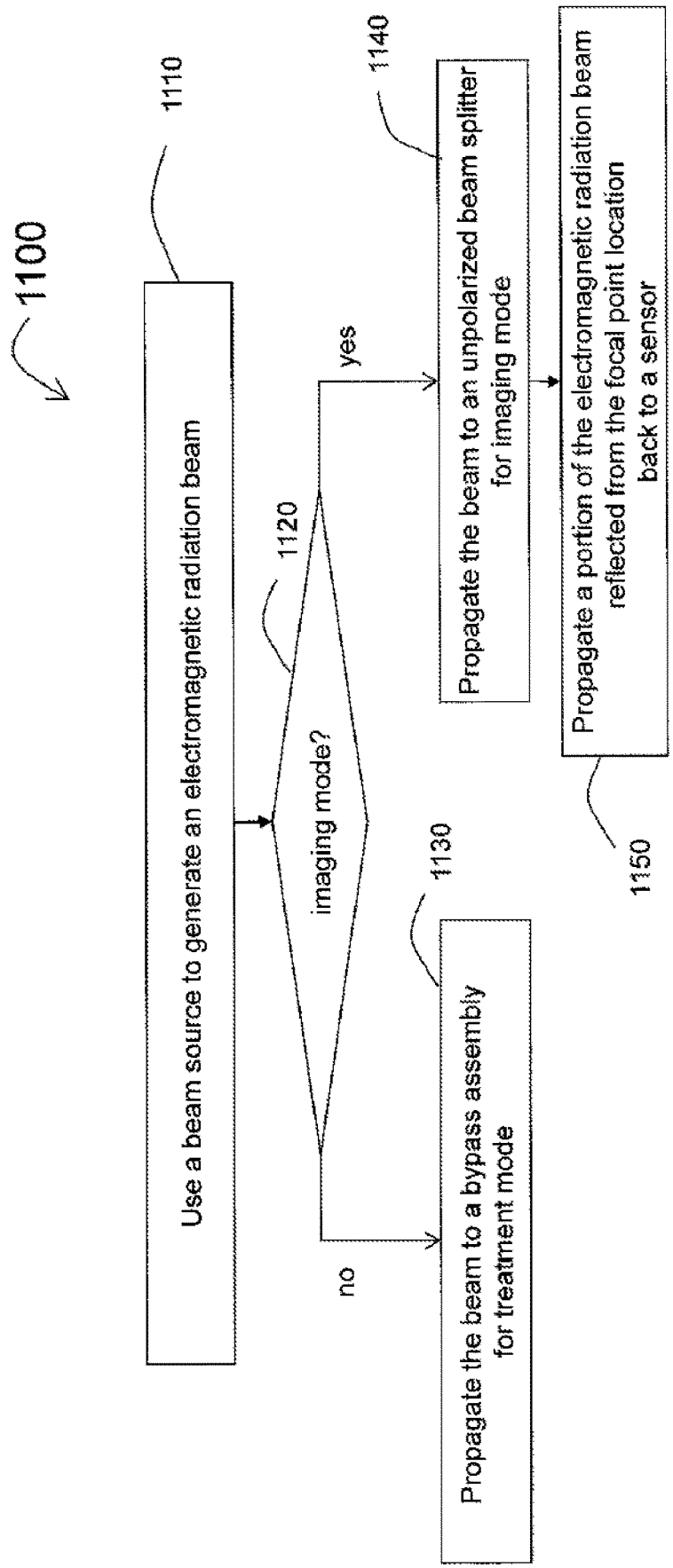
FIG. 21 is a simplified process for imaging and treating an eye according to an embodiment of the invention.

FIG. 21 shows a process 1100 of the laser surgery system 1000 for imaging and treating an eye, e.g., a cornea, according to an embodiment of the invention. The laser surgery system 1000 uses a beam source to generate an electromagnetic radiation beam (Action Block 1110). If the system 1000 is in treatment mode (Decision Block 1120), the system 1000 propagates the electromagnetic radiation beam to a bypass assembly 1014 (Action Block 1130). If the system 1000 is in imaging mode (Decision Block 1120), the system 1000 propagates the electromagnetic radiation beam to a beam-splitter and dump 1048 (Action Block 1140). It is noted that the beam-splitter need only be substantially unpolarized in the returning (i.e. reflected beam). The outgoing (transmitted beam) may already be inherently polarized and the beam-splitter transmission can be either polarization dependent or polarization independent, so long as the correct outgoing beam transmission occurs. In imaging mode, as a portion of the electromagnetic radiation beam is reflected from the focal point location in the eye, the system 1000 propagates a portion of the reflected electromagnetic radiation beam to a sensor 1054 for imaging (Action Block 1150).

Further, while some of the above methods are described as using a wave plate and more specifically a one-quarter wave plate, it should be understood that other variable axis polarization systems may be used. For example, in some embodiments of processes 100 and 400, the laser surgery system 10 may use a spatial light modulator (e.g., a liquid crystal panel), two or more retarding wave plates, a Faraday rotator, a rotating polarizing beam-splitter, and so on.

In some embodiments, knowledge about corneal polarization may be used for other therapeutic applications in which the degree of polarization rotation is an indicator of tissue condition, and could lead to iteration of the planned treatment. For instance, corneal retardance could be an indicator of disease progression such as corneal thinning, or could indicate the strength of corneal tissue, which in turn would be valuable in correctly calculating corneal arcuate incisions, or limbal relaxing incisions used for astigmatic correction.

In many embodiments, one or more measurements of a cornea are used with input parameters to determine locations of incisions of the cornea, such as corneal incisions. The one or more measurements can be obtained in many ways, such as with images used for measuring corneal topography or tomography, or without imaging the eye. One or more additional images can be obtained when the one or more measurements are obtained, and these one or more additional images can be used in combination with the measurements for aligning the measurement coordinates and the cutting coordinates.

In many embodiments, a surface profile of the cornea is measured in one or more of many ways, and may comprise one or more of an anterior corneal surface topography profile, a posterior a corneal surface topography profile, or a corneal thickness profile. In many embodiments, the surface profile comprises a representation of a three dimensional profile and may comprise an extraction of one or more parameters from one or more images, such as an extraction of keratometry values from a corneal topography system or tomography system integrated with the surgical laser. The one or more parameters can be used to determine a tissue treatment pattern on the eye, such as the angular location, depth, arc length and anterior to posterior dimensions of relaxing incisions.

Figure 22:
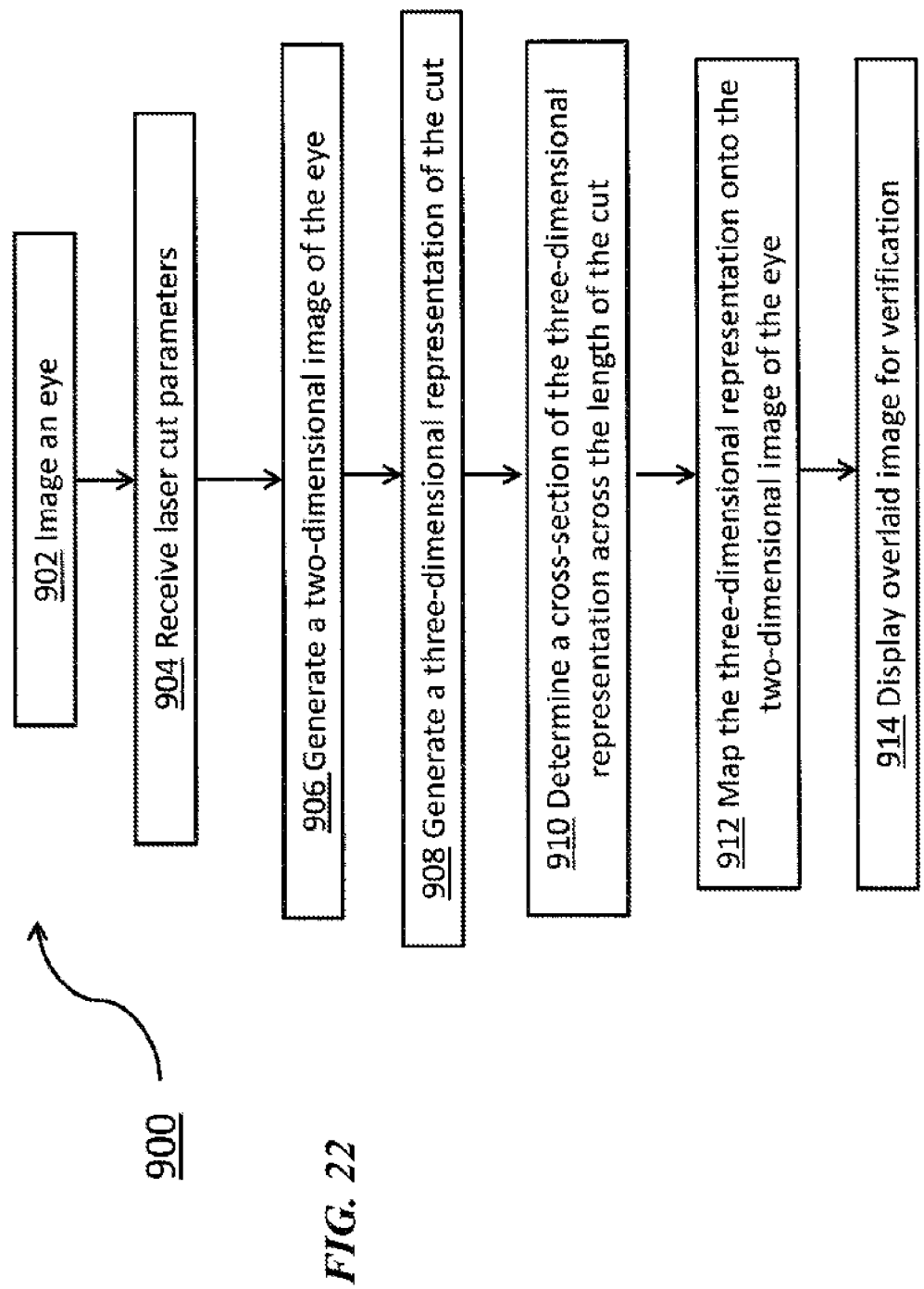
FIG. 22 is a simplified process of imaging an eye with a proposed incision, according to an embodiment of the invention.
Figure 23A:
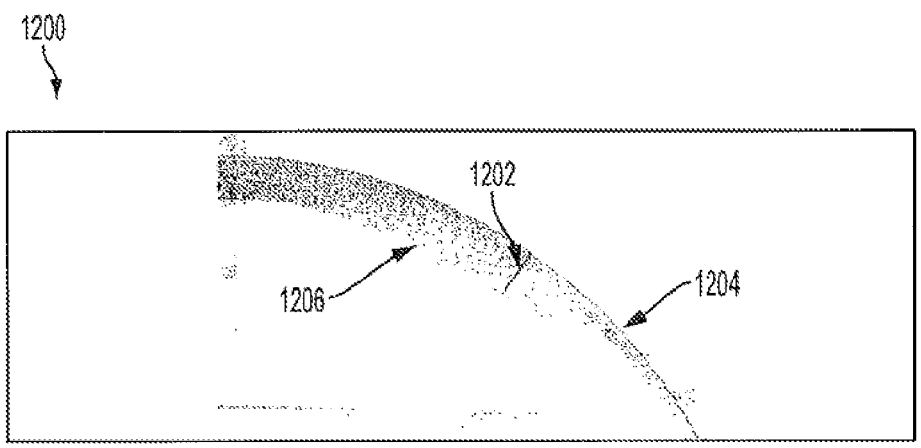
FIGS. 23A and 23B show an exemplary display of an incision review for a cornea of an eye generated according to an embodiment of the invention.
Figure 23B:
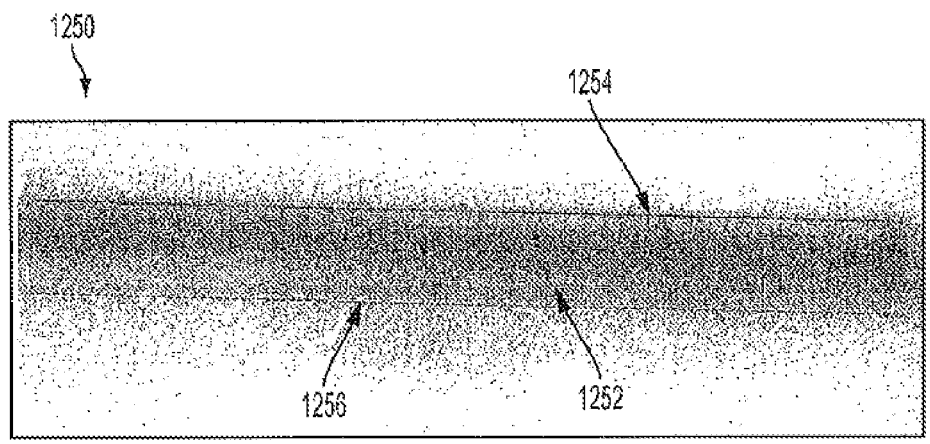

FIG. 22 is a simplified process 900 of imaging an eye with a proposed incision, according to the many embodiments for imaging an eye described herein. FIGS. 23A-23B show an exemplary display of an incision review of a cornea of an eye generated according to an embodiment of the invention. Although FIGS. 22 and 23A-23B are described using an arcuate incision, the laser cut preview images are not limited to arcuate incisions and can be generated for primary and side-port incisions, as well as any other incision in the eye.

The process may start with obtaining an image of the eye as discussed in any of the embodiments herein, such as by a laser surgery system 10 (Action Block 902). A plurality of parameters are then received that define the laser incision (Action Block 904). For instance, the parameters of an arcuate incision cut may include the type of cut, axis (degree), optical zone (mm), length (mm), center method, horizontal spot spacing (μm), vertical spot spacing (μm), pulse energy (μj), anterior density, anterior line distance (μm), central line density, uncut anterior (μm), uncut posterior (μm), and side cut angle (degree). The type of cut may include single, symmetric, asymmetric and toric. The uncut anterior and uncut posterior may also be input as a percentage value and indicate a margin of the cut from the cornea anterior and cornea posterior, respectively. The parameters may be input or predetermined. FIG. 23A illustrates an image 1200 of the cornea including the anterior 1204 and posterior 1206. A preview of an arcuate incision 1202 is overlaid on the cornea image 1200 where the incision 1202 is of the same cross-sectional plane as the cornea image. From FIG. 23A alone, a user is unable to verify that the incision does not penetrate the cornea throughout the entire length of the incision since only one plane of the incision 1202 is shown.

Next, a two-dimensional image of the eye is generated in a plane defined by the intersection of the length and depth of the cut (Action Block 906). In particular, the image is in the plane of the incision axis and an incision length transverse to the incision axis. The image can include the cornea anterior and cornea posterior and may include enhancement to highlight the cornea anterior and cornea posterior, as shown in FIG. 23B and explained in further detail below. Based on the received cut parameters, a three-dimensional representation of the cut is generated such as of a conical surface of an arcuate incision (Action Block 908). From the generated three-dimensional representation of the cut, a three-dimensional cross-section of the conical surface along a length of the cut is determined (Action Block 910). This "along the cut" image is defined as a set of points representing a section of the conical surface including the arcuate incision. In order to display the three-dimensional cross-section on the two-dimensional image of the eye, the "along the cut" image is necessarily distorted, such as by 3D projection, so that the points of the three-dimensional surface are mapped onto the two-dimensional plane of the image (Action Block 912). Alternatively, the set of points in the three-dimensional representation may be set with a common angular value in the conical surface to be in the same column of the two-dimensional image in order to overlay the arcuate incision over the eye. No matter how the three-dimensional representation is displayed on the two-dimensional eye image, the overlaid image is displayed for verification on a display of the system visible to the user (Action Block 914). Alternatively, a processor of the system 10 may perform the verification to determine if the proposed cut crosses the anterior or posterior of the cornea.

FIG. 23B is an exemplary display 1250 of the along the cut image overlaid on the image of the eye that is displayed to a user. The shaded area 1252 represents the proposed cut along the length of the cut. In particular, the cornea anterior 1254 and the cornea posterior 1256 are highlighted by a solid line and dashed line respectively, for a surgeon to verify that the shaded arcuate incision area 1252 does not penetrate the cornea posterior at any point. The arcuate incision 1252 is a projection of the three-dimensional surface onto the two-dimensional eye image that allows a surgeon to visually determine whether the incision will penetrate the posterior surface of the cornea at any point along the cut, instead of just at a single cross-section. The "along the cut" images may be generated using confocal imaging that produces one pixel per laser pulse or by OCT that produces vertical A scans of pixels for each pulse.

While the incision preview image of FIG. 23A displays only one plane of the incision, the incision preview of FIG. 23B displays the proposed incision along the entire length of the cut, thereby allowing a surgeon to more accurately verify whether the proposed cut will cross through the cornea at any point along the length of the cut.

In an embodiment, the laser surgery system 10 receives a plurality of parameters corresponding to the treatment planning, generates a three-dimensional representation of the treatment planning, maps the three-dimensional representation onto the image of the eye, and displays the mapped image for the treatment planning. The treatment planning includes an arcuate incision. The system can verify that the arcuate incision lies within the cornea. The received parameters may include a treatment axis and a treatment length transverse to the axis. The image of the eye is in a plane of the treatment axis and the treatment length. The three-dimensional representation is mapped onto the image of the eye by projecting the three-dimensional representation onto a two-dimensional space. The displayed image comprises a cornea of the eye including an anterior and posterior. The anterior and posterior of the cornea are highlighted. The treatment planning may also include one of a primary and side-port incision.

In an embodiment, the laser surgery system 10 focuses a first electromagnetic radiation beam to a focal point at a location in the eye and focuses a second electromagnetic radiation beam to a focal point at the location in the eye. A first intensity signal is generated indicative of an intensity of electromagnetic radiation reflected from the eye in response to the step of focusing the first electromagnetic radiation beam. A second intensity signal is generated indicative of an intensity of electromagnetic radiation reflected from the eye in response to the step of focusing the second electromagnetic radiation beam. One or more images of the eye are generated with the first and second intensity signals for treatment planning. A plurality of parameters are received corresponding to the treatment planning. A three-dimensional representation of the treatment planning is generated. The three-dimensional representation is mapped onto the image of the eye. The mapped image is displayed for the treatment planning.

In an embodiment, the laser surgery system includes a laser beam source configured to output a beam along a beam path toward the eye. A beam scanner is configured to direct the outputted beam to a plurality of locations in the eye. A sensor is positioned to receive reflected electromagnetic radiation from the eye. A processor is configured to generate one or more images of the eye with the first and second intensity signals for treatment planning. A user input device is configured to receive a plurality of parameters corresponding to the treatment planning. The processor generates a three-dimensional representation of the treatment planning, maps the three-dimensional representation onto the image of the eye. A display is configured to display the mapped image for the treatment planning.

Figure 24:
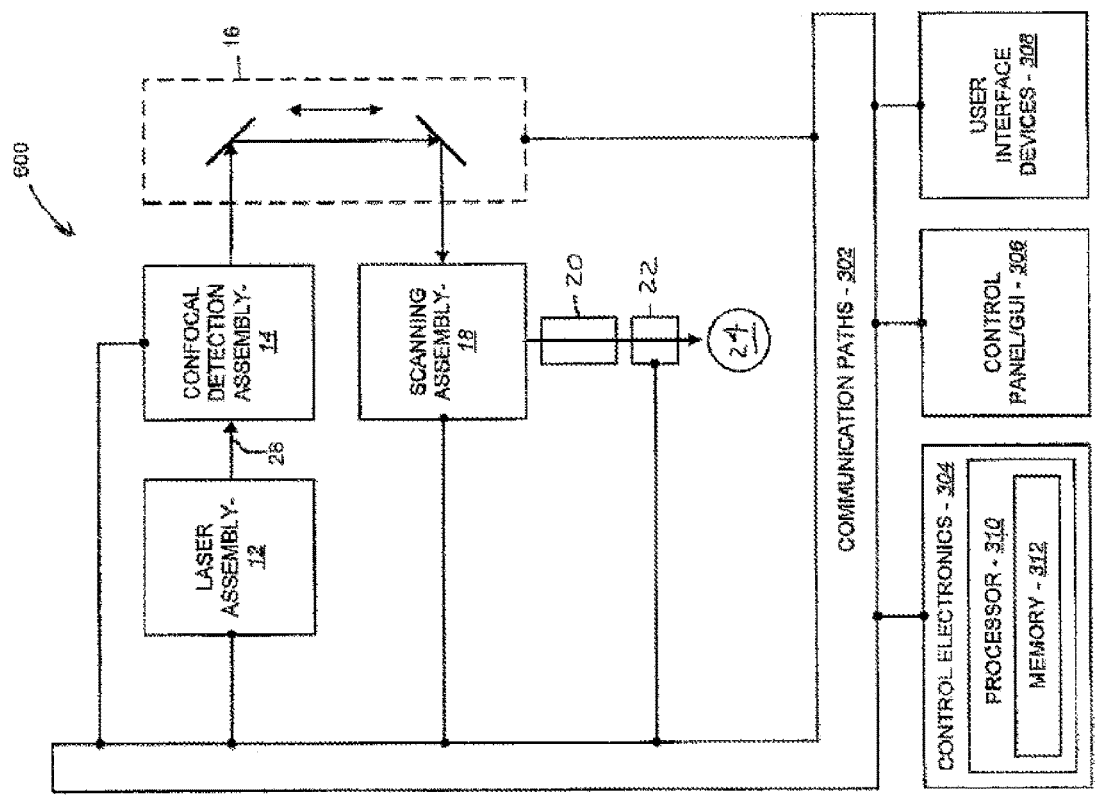
FIG. 24 is another schematic diagram of the laser surgery system of FIG. 1 according to an embodiment of the invention.
Figure 25:
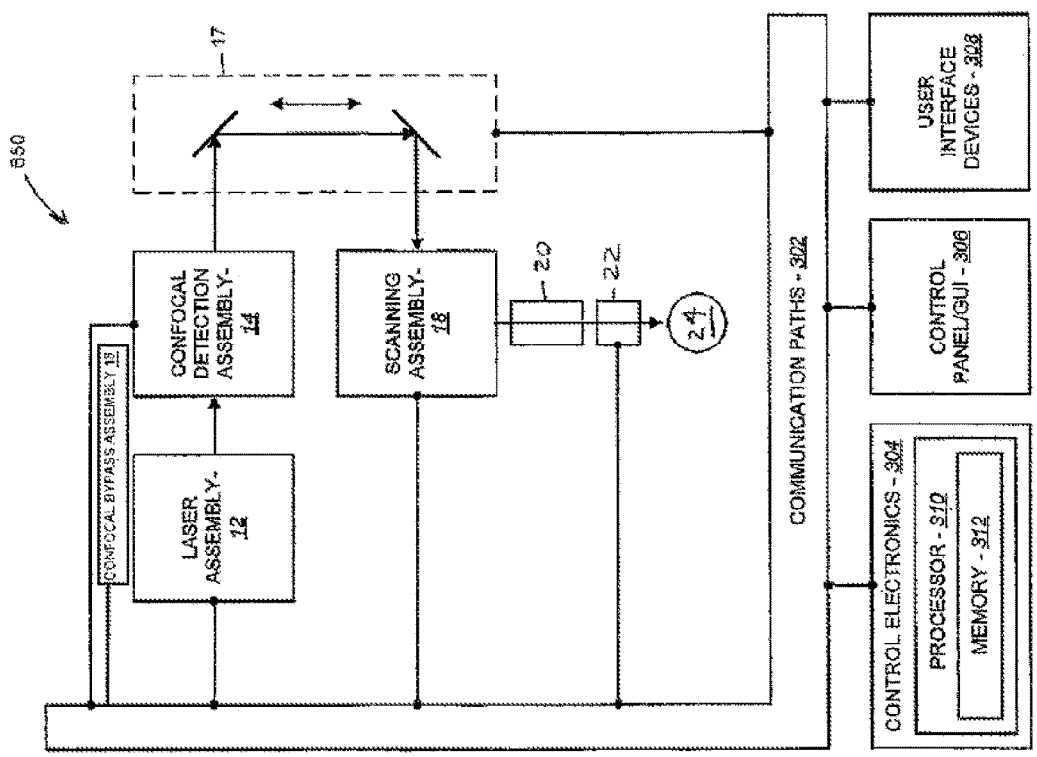
FIG. 25 is another schematic diagram of the laser surgery system of FIG. 10A and FIG. 10B according to an embodiment of the invention.

FIGS. 24 and 25 schematically illustrate a laser surgery system 600 and 650, respectively according to many embodiments. The laser surgery system 600 in FIG. 24 includes the laser assembly 12, the confocal detection assembly 14, the free-floating mechanism 16, the scanning assembly 18, the objective lens assembly 20, the patient interface 22, communication paths 302, control electronics 304, control panel/graphical user interface (GUI) 306, and user interface devices 308. The control electronics 304 includes processor 310, which includes memory 312. The patient interface 22 is configured to interface with a patient 24. The control electronics 304 is operatively coupled via the communication paths 302 with the laser assembly 12, the confocal detection assembly 14, the free-floating mechanism 16, the scanning assembly 18, the control panel/GUI 306, and the user interface devices 308. The laser surgery system 650 in FIG. 25 additionally includes the confocal bypass assembly 15, and substitutes the transfer optical path 17 for the free floating-mechanism 16. It should be noted, however, that free floating assembly 16 could also replace the transfer optical path 17 in laser surgery system 650.

The scanning assembly 18 can include a Z-scan device and an XY-scan device. The laser surgery system 300 may be configured to focus the electromagnetic radiation beam 28 to a focal point that is scanned in three dimensions. The Z-scan device may be operable to vary the location of the focal point in the direction of propagation of the beam 28. The XY-scan device may be operable to scan the location of the focal point in two dimensions transverse to the direction of propagation of the beam 28. Accordingly, the combination of the Z-scan device and the XY-scan device can be operated to controllably scan the focal point of the beam in three dimensions, including: within a tissue, e.g., eye tissue, of the patient 24. The scanning assembly 18 may be supported by the free-floating mechanism 16, which may accommodate patient movement, induced movement of the scanning assembly 18 relative to the laser assembly 12 and the confocal detection assembly 14 in three dimensions.

The patient interface 22 is coupled to the patient 24 such that the patient interface 22, the objective lens assembly 20, and the scanning assembly 18 move in conjunction with the patient 24. For example, in many embodiments, the patient interface 22 employs a suction ring that is vacuum attached to an eye of the patient 24. The suction ring may be coupled to the patient interface 22, for example, using vacuum.

The control electronics 304 controls the operation of and/or can receive input from the laser assembly 12, the confocal detection assembly 14, the free-floating assembly 16, the scanning assembly 18, the patient interface 22, the control panel/GUI 306, and the user interface devices 308 via the communication paths 302. The communication paths 302 can be implemented in any suitable configuration, including any suitable shared or dedicated communication paths between the control electronics 304 and the respective system components.

The control electronics 304 can include any suitable components, such as one or more processors, one or more field-programmable gate array (FPGA), and one or more memory storage devices. In many embodiments, the control electronics 304 controls the control panel/GUI 306 to provide for pre-procedure planning according to user specified treatment parameters as well as to provide user control over the laser eye surgery procedure.

The control electronics 304 can include a processor/controller 310 that is used to perform calculations related to system operation and provide control signals to the various system elements. A computer readable medium 312 is coupled to the processor 310 in order to store data used by the processor and other system elements. The processor 310 interacts with the other components of the system as described more fully throughout the present specification. In an embodiment, the memory 312 can include a look up table that can be utilized to control one or more components of the laser system surgery system 300.

The processor 310 can be a general purpose microprocessor configured to execute instructions and data such as a processor manufactured by the Intel Corporation of Santa Clara, California It can also be an Application Specific Integrated Circuit (ASIC) that embodies at least part of the instructions for performing the method according to the embodiments of the present disclosure in software, firmware and/or hardware. As an example, such processors include dedicated circuitry, ASICs, combinatorial logic, other programmable processors, combinations thereof, and the like.

The memory 312 can be local or distributed as appropriate to the particular application. Memory 312 can include a number of memories including a main random access memory (RAM) for storage of instructions and data during program execution and a read only memory (ROM) in which fixed instructions are stored. Thus, the memory 312 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 308 can include any suitable user input/output device suitable to provide user input to the control electronics 304. For example, the user interface devices 308 can include devices such as a touch-screen display/input device, a keyboard, a footswitch, a keypad, a patient interface radio frequency identification (RFID) reader, an emergency stop button, a key switch, and so on.

The embodiments disclosed herein are well suited for combination with prior laser surgery systems, such as the Catalys Precision Laser System commercially available from Optimedica, and similar systems. Such systems can be modified in accordance with the teachings disclosed herein and to more accurately measure and treat the eye.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The confocal bypass assembly has been described here in relation to a specific laser eye surgery system. The bypass assemblies, such as those illustrated in FIG. 13, and as described herein, may be generally applied to other laser surgery systems in cases where it may be advantageous to separate an imaging mode from a treatment mode in specified surgery fields. They may also be applicable to non-surgical systems and methods, such as various materials processing systems, and micromachining systems.

Other embodiments include and incorporate imaging systems having laser assemblies, confocal detection assemblies, and systems that accommodate patient movement, including the eye interface, scanning assembly, free-floating mechanism described in U.S. Patent Application No. 61/780,736, filed Mar. 13, 2013 and U.S. patent application Ser. No. 14/191,095, filed Feb. 26, 2014, which takes priority to U.S. Patent Application No. 61/780,736. and U.S. Patent Application No. 61/780,881, filed Mar. 13, 2013 and U.S. patent application Ser. No. 14/190,827, filed Feb. 26, 2014, which takes priority to U.S. Patent Application No. 61/780,881.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention. As used herein, the terms first and second are used to describe structures and methods without limitation as to the order of the structures and methods which can be in any order, as will be apparent to a person of ordinary skill in the art based on the teachings provided herein.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. A method of imaging an eye having a cornea, the cornea having a first region with a first birefringence and a second region with a second birefringence, the method comprising:
   directing a first electromagnetic radiation beam through the first region of the cornea to a first location in the eye, the first electromagnetic radiation beam having a first polarization;
   directing a second electromagnetic radiation beam through the second region of the cornea to a second location in the eye, the second electromagnetic radiation beam having a second polarization different than the first polarization; and
   generating a single composite image of the eye encompassing the first and second locations using electromagnetic radiation signals reflected from the eye in response to the steps of directing the first and second electromagnetic radiation beams, wherein the single composite image includes a first image area corresponding to the first location in the eye and a second image area corresponding to the second location in the eye, wherein the first image area is generated using only a first electromagnetic radiation signal reflected from the first location in the eye in response to the step of directing the first electromagnetic radiation beam, and the second image area is generated using only a second electromagnetic radiation signal reflected from the second location in the eye in response to the step of directing the second electromagnetic radiation beam.

* * * * *